United States Patent [19]

Tsuchiya et al.

[11] Patent Number: 6,121,423
[45] Date of Patent: Sep. 19, 2000

[54] RESHAPED HUMAN ANTIBODY TO HUMAN INTERLEUKIN-6

[75] Inventors: Masayuki Tsuchiya; Koh Sato; Yuichi Hirata, all of Gotenba, Japan

[73] Assignee: Chugai Seiyaku Kabushiki Kaisha, Tokyo, Japan

[21] Appl. No.: 09/205,231

[22] Filed: Dec. 4, 1998

Related U.S. Application Data

[62] Division of application No. 08/553,501, filed as application No. PCT/JP94/00859, May 30, 1994, Pat. No. 5,856,135.

[30] Foreign Application Priority Data

May 31, 1993 [JP] Japan ................................. 5-129787

[51] Int. Cl.$^7$ ............................. C07K 16/00; C12P 21/08
[52] U.S. Cl. ................................. 530/387.1; 530/387.3; 530/388.1; 530/388.23
[58] Field of Search .................... 530/387.1, 387.3, 530/388.1, 388.23

[56] References Cited

FOREIGN PATENT DOCUMENTS 20-5553   5/1993   China .
0 399 429  11/1990  European Pat. Off. .
0 628 639  12/1994  European Pat. Off. .

OTHER PUBLICATIONS

Saito et al., "Suppression of Plasmacytosis Arisis In IL–6 Transgenic Mouse by Administration of Anti–Human IL–6 Monoclonal Antibody", Jp. Soc. of Immun. vol. 21, (1991), pp. 1–4/Eng. Translation.

*Primary Examiner*—Mark Navarro
*Attorney, Agent, or Firm*—Foley & Lardner

[57] ABSTRACT

A reshaped antibody comprising:
(A) L chains comprising:
   (1) a human C region, and
   (2) an L chain V region comprising human L chain FRs and L chain CDRs of a mouse monoclonal antibody; and
(B) H chains comprising:
   (1) a human H chain C region, and
   (2) an H chain V region comprising human H chain FRs, and H chain CDRs of a mouse monoclonal antibody to human IL-6. Since the major portions of the reshaped human antibody are derived from human, and the mouse CDRs are less immunogenic, then the present reshaped human antibody is less immunogenic, and therefore inhibits information transfer by IL-6, and is promising as a therapeutic agent for diseases caused by IL-6.

3 Claims, 10 Drawing Sheets

FIG. 10

BINDING INHIBITION ASSAY

- △ CHIMERIC
- ○ RVLa/RVHa
- ● RVLa/RVHb
- □ RVLb/RVHa
- ■ RVLb/RVHb
- ▲ MOUSE SK2
- ---△--- CHIMERIC (NTS)

SEQUENCE LISTING (1) GENERAL INFORMATION:

(iii) NUMBER OF SEQUENCES: 91

(2) INFORMATION FOR SEQ ID NO:1:

(i) SEQUENCE CHARACTERISTICS:
    (A) LENGTH: 40 base pairs
    (B) TYPE: nucleic acid
    (C) STRANDEDNESS: single
    (D) TOPOLOGY: linear (xi) SEQUENCE DESCRIPTION: SEQ ID NO:1:

ACTAGTCGAC ATGAAGTTGC CTGTTAGGCT GTTGGTGCTG                          40

(2) INFORMATION FOR SEQ ID NO:2:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:2:

ACTAGTCGAC ATGGAGWCAG ACACACTCCT GYTATGGGT                           39

(2) INFORMATION FOR SEQ ID NO:3:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:3:

ACTAGTCGAC ATGAGTGTGC TCACTCAGGT CCTGGSGTTG                          40

(2) INFORMATION FOR SEQ ID NO:4:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:4:

ACTAGTCGAC ATGAGGRCCC CTGCTCAGWT TYTTGGMWTC TTG                      43

(2) INFORMATION FOR SEQ ID NO:5:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:5:

ACTAGTCGAC ATGGATTTWC AGGTGCAGAT TWTCAGCTTC                          40

(2) INFORMATION FOR SEQ ID NO:6:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:6:

ACTAGTCGAC ATGAGGTKCY YTGYTSAGYT YCTGRGG                             37

(2) INFORMATION FOR SEQ ID NO:7:

(i) SEQUENCE CHARACTERISTICS:
    (A) LENGTH: 41 base pairs
    (B) TYPE: nucleic acid
    (C) STRANDEDNESS: single
    (D) TOPOLOGY: linear (xi) SEQUENCE DESCRIPTION: SEQ ID NO:7:

ACTAGTCGAC ATGGGCWTCA AGATGGAGTC ACAKWYYCWG G                                41

(2) INFORMATION FOR SEQ ID NO:8:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:8:

ACTAGTCGAC ATGTGGGAY CTKTTTYCMM TTTTTCAATT G                                 41

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:9:

ACTAGTCGAC ATGGTRTCCW CASCTCAGTT CCTTG                                       35

(2) INFORMATION FOR SEQ ID NO:10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:10:

ACTAGTCGAC ATGTATATAT GTTTGTTGTC TATTTCT                                     37

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:11:

ACTAGTCGAC ATGGAAGCCC CAGCTCAGCT TCTCTTCC                                    38

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:12:

GGATCCCGGG TGGATGGTGG GAAGATG                                                27

(2) INFORMATION FOR SEQ ID NO:13:

(i) SEQUENCE CHARACTERISTICS:

(A) LENGTH: 37 base pairs
    (B) TYPE: nucleic acid
    (C) STRANDEDNESS: single
    (D) TOPOLOGY: linear (xi) SEQUENCE DESCRIPTION: SEQ ID NO:13:

ACTAGTCGAC ATGAAATGCA GCTGGGTCAT STTCTTC    37

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:14:

ACTAGTCGAC ATGGGATGGA GCTRTATCAT SYTCTT    36

(2) INFORMATION FOR SEQ ID NO:15:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:15:

ACTAGTCGAC ATGAAGWTGT GGTTAAACTG GGTTTTT    37

(2) INFORMATION FOR SEQ ID NO:16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:16:

ACTAGTCGAC ATGRACTTTG GGYTCAGCTT GRTTT    35

(2) INFORMATION FOR SEQ ID NO:17:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:17:

ACTAGTCGAC ATGGACTCCA GGCTCAATTT AGTTTTCCTT    40

(2) INFORMATION FOR SEQ ID NO:18:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:18:

ACTAGTCGAC ATGGCTGTCY TRGSGCTRCT CTTCTGC    37

(2) INFORMATION FOR SEQ ID NO:19:

(i) SEQUENCE CHARACTERISTICS:
        (A) LENGTH: 36 base pairs (B) TYPE: nucleic acid
        (C) STRANDEDNESS: single
        (D) TOPOLOGY: linear (xi) SEQUENCE DESCRIPTION: SEQ ID NO:19:

ACTAGTCGAC ATGGRATGGA GCKGGRTCTT TMTCTT                                    36

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:20:

ACTAGTCGAC ATGAGAGTGC TGATTCTTTT GTG                                       33

(2) INFORMATION FOR SEQ ID NO:21:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:21:

ACTAGTCGAC ATGGMTTGGG TGTGGAMCTT GCTATTCCTG                                40

(2) INFORMATION FOR SEQ ID NO:22:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:22:

ACTAGTCGAC ATGGGCAGAC TTACATTCTC ATTCCTG                                   37

(2) INFORMATION FOR SEQ ID NO:23:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:23:

ACTAGTCGAC ATGGATTTTG GGCTGATTTT TTTTATTG                                  38

(2) INFORMATION FOR SEQ ID NO:24:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:24:

ACTAGTCGAC ATGATGGTGT TAAGTCTTCT GTACCTG                                   37

(2) INFORMATION FOR SEQ ID NO:25:

(i) SEQUENCE CHARACTERISTICS:
        (A) LENGTH: 28 base pairs
        (B) TYPE: nucleic acid (C) STRANDEDNESS: single
        (D) TOPOLOGY: linear (xi) SEQUENCE DESCRIPTION: SEQ ID NO:25:

GGATCCCGGG CCAGTGGATA GACAGATG                                              28

(2) INFORMATION FOR SEQ ID NO:26:

(i) SEQUENCE CHARACTERISTICS:
        (A) LENGTH: 379 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..378

(ix) FEATURE:
        (A) NAME/KEY: mat_peptide
        (B) LOCATION: 1..378

(xi) SEQUENCE DESCRIPTION: SEQ ID NO:26:

```
ATG AGT GTG CTC ACT CAG GTC CTG GGG TTG CTG CTG CTG TGG CTT ACA        48
Met Ser Val Leu Thr Gln Val Leu Gly Leu Leu Leu Leu Trp Leu Thr
 1               5                  10                  15

GAT GCC AGA TGT GAC ATC CAG ATG ACT CAG TCT CCA GCC TCC CTA TCT        96
Asp Ala Arg Cys Asp Ile Gln Met Thr Gln Ser Pro Ala Ser Leu Ser
            20                  25                  30

GTA TCA GTG GGA GAA ACT GTC ACC ATC ACA TGT CGA GCA AGT GAG AAT       144
Val Ser Val Gly Glu Thr Val Thr Ile Thr Cys Arg Ala Ser Glu Asn
        35                  40                  45

ATT TAC AGT AAT TTA GCA TGG TAT CAG CAG AAA CAG GGA AAA TCT CCT       192
Ile Tyr Ser Asn Leu Ala Trp Tyr Gln Gln Lys Gln Gly Lys Ser Pro
    50                  55                  60

CAG CTC CTG GTC TAT GCC GCA ACA TAC TTA GCA GAT GGT GTG CCA TCA       240
Gln Leu Leu Val Tyr Ala Ala Thr Tyr Leu Ala Asp Gly Val Pro Ser
 65                  70                  75                  80

AGG TTC AGT GGC AGT GGA TCA GGC ACA CAG TAT TCC CTA AAG ATC AAC       288
Arg Phe Ser Gly Ser Gly Ser Gly Thr Gln Tyr Ser Leu Lys Ile Asn
                 85                  90                  95

AGC CTG CAG TCT GAA GAT TTT GGG AGT TAT TAC TGT CAA CAT TTT TGG       336
Ser Leu Gln Ser Glu Asp Phe Gly Ser Tyr Tyr Cys Gln His Phe Trp
            100                 105                 110

GGT ACT CCT CCG TTC GGC TCG GGG ACA AAG TTG GAA ATA AAA               378
Gly Thr Pro Pro Phe Gly Ser Gly Thr Lys Leu Glu Ile Lys
        115                 120                 125

C                                                                     379
```

(2) INFORMATION FOR SEQ ID NO:27:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:27:

```
Met Ser Val Leu Thr Gln Val Leu Gly Leu Leu Leu Leu Trp Leu Thr
 1               5                  10                  15

Asp Ala Arg Cys Asp Ile Gln Met Thr Gln Ser Pro Ala Ser Leu Ser
            20                  25                  30

Val Ser Val Gly Glu Thr Val Thr Ile Thr Cys Arg Ala Ser Glu Asn
```

```
                35                  40                  45
Ile Tyr Ser Asn Leu Ala Trp Tyr Gln Gln Lys Gln Gly Lys Ser Pro
     50                  55                  60

Gln Leu Leu Val Tyr Ala Ala Thr Tyr Leu Ala Asp Gly Val Pro Ser
 65                  70                  75                  80

Arg Phe Ser Gly Ser Gly Ser Gly Thr Gln Tyr Ser Leu Lys Ile Asn
                 85                  90                  95

Ser Leu Gln Ser Glu Asp Phe Gly Ser Tyr Tyr Cys Gln His Phe Trp
                100                 105                 110

Gly Thr Pro Pro Phe Gly Ser Gly Thr Lys Leu Glu Ile Lys
                115                 120                 125

(2) INFORMATION FOR SEQ ID NO:28:

(i) SEQUENCE CHARACTERISTICS:
        (A) LENGTH: 418 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..417

(ix) FEATURE:
        (A) NAME/KEY: mat_peptide
        (B) LOCATION: 1..417

(xi) SEQUENCE DESCRIPTION: SEQ ID NO:28:

ATG GGC AGA CTT ACA TTC TCA TTC CTG CTA CTG ATT GTC CCT GCA TAT      48
Met Gly Arg Leu Thr Phe Ser Phe Leu Leu Leu Ile Val Pro Ala Tyr
 1               5                  10                  15

GTC CTG TCC CAG GTT ACT CTG AAA GAG TCT GGC CCT GGG ATA TTG CAG      96
Val Leu Ser Gln Val Thr Leu Lys Glu Ser Gly Pro Gly Ile Leu Gln
                 20                  25                  30

CCC TCC CAG ACC CTC AGT CTG ACT TGT TCT TTC TCT GGT TTT TCA CTG     144
Pro Ser Gln Thr Leu Ser Leu Thr Cys Ser Phe Ser Gly Phe Ser Leu
             35                  40                  45

AAC ACT TCT GGT ATG ACC GTA GGC TGG ATT CGT CAG CCT TCA GGG AAG     192
Asn Thr Ser Gly Met Thr Val Gly Trp Ile Arg Gln Pro Ser Gly Lys
         50                  55                  60

GGT CTG GAG TGG CTG GCA CAC ATT TGG TGG AAT GAT GAT AAG TAC TAT     240
Gly Leu Glu Trp Leu Ala His Ile Trp Trp Asn Asp Asp Lys Tyr Tyr
 65                  70                  75                  80

AAC CCA GCC CTG AAA GGC CGG CTC ACA ATC TCC AAG GAT ACC TCC AAC     288
Asn Pro Ala Leu Lys Gly Arg Leu Thr Ile Ser Lys Asp Thr Ser Asn
                 85                  90                  95

AAC CAG GTA TTC CTC AAG ATC GCC AGT GTG GTC ACT GCA GAT ACT GCC     336
Asn Gln Val Phe Leu Lys Ile Ala Ser Val Val Thr Ala Asp Thr Ala
                100                 105                 110

ACA TAC TAC TGT GCT CGA ATG GAG GAT TAC GAC GAA GCT ATG GAC TAC     384
Thr Tyr Tyr Cys Ala Arg Met Glu Asp Tyr Asp Glu Ala Met Asp Tyr
             115                 120                 125

TGG GGT CAA GGA ACC TCA GTC ACC GTC TCC TCA G                       418
Trp Gly Gln Gly Thr Ser Val Thr Val Ser Ser
         130                 135

(2) INFORMATION FOR SEQ ID NO:29:

(i) SEQUENCE CHARACTERISTICS:
        (A) LENGTH: 139 amino acids
        (B) TYPE: amino acid
        (D) TOPOLOGY: linear
```

(ii) MOLECULE TYPE: protein (xi) SEQUENCE DESCRIPTION: SEQ ID NO:29:

| Met | Gly | Arg | Leu | Thr | Phe | Ser | Phe | Leu | Leu | Leu | Ile | Val | Pro | Ala | Tyr |
|---|---|---|---|---|---|---|---|---|---|---|---|---|---|---|---|
| 1 | | | | 5 | | | | | 10 | | | | | 15 | |

| Val | Leu | Ser | Gln | Val | Thr | Leu | Lys | Glu | Ser | Gly | Pro | Gly | Ile | Leu | Gln |
|---|---|---|---|---|---|---|---|---|---|---|---|---|---|---|---|
| | | | 20 | | | | | 25 | | | | | 30 | | |

| Pro | Ser | Gln | Thr | Leu | Ser | Leu | Thr | Cys | Ser | Phe | Ser | Gly | Phe | Ser | Leu |
|---|---|---|---|---|---|---|---|---|---|---|---|---|---|---|---|
| | | | 35 | | | | | 40 | | | | | 45 | | |

| Asn | Thr | Ser | Gly | Met | Thr | Val | Gly | Trp | Ile | Arg | Gln | Pro | Ser | Gly | Lys |
|---|---|---|---|---|---|---|---|---|---|---|---|---|---|---|---|
| | 50 | | | | | 55 | | | | | 60 | | | | |

| Gly | Leu | Glu | Trp | Leu | Ala | His | Ile | Trp | Trp | Asn | Asp | Asp | Lys | Tyr | Tyr |
|---|---|---|---|---|---|---|---|---|---|---|---|---|---|---|---|
| 65 | | | | | 70 | | | | | 75 | | | | | 80 |

| Asn | Pro | Ala | Leu | Lys | Gly | Arg | Leu | Thr | Ile | Ser | Lys | Asp | Thr | Ser | Asn |
|---|---|---|---|---|---|---|---|---|---|---|---|---|---|---|---|
| | | | | 85 | | | | | 90 | | | | | 95 | |

| Asn | Gln | Val | Phe | Leu | Lys | Ile | Ala | Ser | Val | Val | Thr | Ala | Asp | Thr | Ala |
|---|---|---|---|---|---|---|---|---|---|---|---|---|---|---|---|
| | | | | 100 | | | | | 105 | | | | | 110 | |

| Thr | Tyr | Tyr | Cys | Ala | Arg | Met | Glu | Asp | Tyr | Asp | Glu | Ala | Met | Asp | Tyr |
|---|---|---|---|---|---|---|---|---|---|---|---|---|---|---|---|
| | | | 115 | | | | | 120 | | | | | 125 | | |

| Trp | Gly | Gln | Gly | Thr | Ser | Val | Thr | Val | Ser | Ser |
|---|---|---|---|---|---|---|---|---|---|---|
| | 130 | | | | | 135 | | | | |

(2) INFORMATION FOR SEQ ID NO:30:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:30:

CCTGGATCCA CTCACGTTTT ATTTCCAACT TTGTC                    35

(2) INFORMATION FOR SEQ ID NO:31:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:31:

GATAAGCTTG CCGCCACCAT GAGTGTGCTC ACTCAG                   36

(2) INFORMATION FOR SEQ ID NO:32:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:32:

GATAAGCTTG CCGCCACCAT GGGCAGACTT ACATTC                   36

(2) INFORMATION FOR SEQ ID NO:33:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:33:

TGTTGGATCC ACTCACCTGA AGAGACAGTG ACTGAGGTTC                40

(2) INFORMATION FOR SEQ ID NO:34:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:34:

CAGAAGTGGA CAGTGAAAAA CCAGA                                25

(2) INFORMATION FOR SEQ ID NO:35:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:35:

TTTTTCACTG TCCACTTCTG GTATGAC                              27

(2) INFORMATION FOR SEQ ID NO:36:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:36:

AACAGCTATG ACCATGA                                         17

(2) INFORMATION FOR SEQ ID NO:37:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:37:

GAATTCGGAT CCACTCACGT TTGATT                               26

(2) INFORMATION FOR SEQ ID NO:38:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:38:

GAATATTTAC AGTAATTTAG CATGGTACCA GCAGAAGCC                 39

(2) INFORMATION FOR SEQ ID NO:39:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:39:

TGCTGATCTA CGCCGCAACA TACTTAGCAG ATGGTGTGCC AAGCA                    45

(2) INFORMATION FOR SEQ ID NO:40:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:40:

TTGGGGTACT CCTCCGTTCT GGCCAAGGGA CCAAGGT                              37

(2) INFORMATION FOR SEQ ID NO:41:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:41:

TTACTGTAAA TATTCTCACT TGCTCTACAG GTGATGGTCA C                         41

(2) INFORMATION FOR SEQ ID NO:42:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:42:

ACCATCTGCT AAGTATGTTG CGTCGTAGAT CAGCAGCTTT GGAGC                     45

(2) INFORMATION FOR SEQ ID NO:43:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:43:

CGGAGGAGTA CCCCAAAAAT GTTGGCAGTA GTAGGT                               36

(2) INFORMATION FOR SEQ ID NO:44:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:44:

GGTACCGACT ACACCTTCAC CATCAGCAGC C                                    31

(2) INFORMATION FOR SEQ ID NO:45:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:45:

```
GGTGAAGGTG TAGTCGGTAC CGCTACCGCT A                                    31

(2) INFORMATION FOR SEQ ID NO:46:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (xi) SEQUENCE DESCRIPTION: SEQ ID NO:46:

GATAAGCTTG CCACCATGGA CTGGACCTGG AGGGTCTTCT TCTTGCTGGC TGTAGCTCCA      60

CGTGCTCACT CCCAAGTGAC TCTGAGGGAG TCTGG                                95

(2) INFORMATION FOR SEQ ID NO:47:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (xi) SEQUENCE DESCRIPTION: SEQ ID NO:47:

AGTACTTAAT GAGAAGCCAG AGAAGGTGCA GGTGAGTGTC AGAGTCTGTG TAGGTCTCAC      60

AAGGGCAGGT CCAGACTCCC TCAGAGTCAC TTG                                  93

(2) INFORMATION FOR SEQ ID NO:48:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (xi) SEQUENCE DESCRIPTION: SEQ ID NO:48:

TTCTCTGGCT TCTCATTAAG TACTTCTGGT ATGACCGTAG GCTGGATTCG CCAACCTCCT      60

GGAGAGGCAC TGGAGTGGCT GGCACACATT TGGTG                                95

(2) INFORMATION FOR SEQ ID NO:49:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (xi) SEQUENCE DESCRIPTION: SEQ ID NO:49:

CTGGTTCTTG GATGTGTCTT TGGAGACGGC CAGTCGGCCT TCAGGGCAG GGTTATAGTA       60

CTTATCATCA TTCCACCAAA TGTGTGCCAG CCACTC                               96

(2) INFORMATION FOR SEQ ID NO:50:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (xi) SEQUENCE DESCRIPTION: SEQ ID NO:50:

TCCAAAGACA CATCCAAGAA CCAGGTTGTC CTGTCCATGA ACACCGTGGG TCCCGGGGAC      60

ACAGCCACAT ATTACTGTGC AAGAATGGAG GATTACGA                             98
```

(2) INFORMATION FOR SEQ ID NO:51:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (xi) SEQUENCE DESCRIPTION: SEQ ID NO:51:

```
GTCGGATCCA CTCACCTGAG GAGACGGTGA CCAGAATCCC TTGGCCCCAG TAGTCCATAG      60

CTTCGTCGTA ATCCTCCATT CTTGCACAGT AATA                                 94
```

(2) INFORMATION FOR SEQ ID NO:52:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:52:

```
TTCTCATTAA ATACTTCTGG TATGACCGTA                                      30
```

(2) INFORMATION FOR SEQ ID NO:53:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:53:

```
ACCAGAAGTA TTTAATGAGA AGCCAGAGAA G                                    31
```

(2) INFORMATION FOR SEQ ID NO:54:

(i) SEQUENCE CHARACTERISTICS:
        (A) LENGTH: 376 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..375

(ix) FEATURE:
        (A) NAME/KEY: mat_peptide
        (B) LOCATION: 1..375

(xi) SEQUENCE DESCRIPTION: SEQ ID NO:54:

```
ATG GGA TGG AGC TGT ATC ATC CTC TTC TTG GTA GCA ACA GCT ACA GGT       48
Met Gly Trp Ser Cys Ile Ile Leu Phe Leu Val Ala Thr Ala Thr Gly
 1               5                  10                  15

GTC CAC TCC GAC ATC CAG ATG ACC CAG AGC CCA AGC AGC CTG AGC GCC       96
Val His Ser Asp Ile Gln Met Thr Gln Ser Pro Ser Ser Leu Ser Ala
                20                  25                  30

AGC GTG GGT GAC AGA GTG ACC ATC ACC TGT AGA GCA AGT GAG AAT ATT      144
Ser Val Gly Asp Arg Val Thr Ile Thr Cys Arg Ala Ser Glu Asn Ile
            35                  40                  45

TAC AGT AAT TTA GCA TGG TAC CAG CAG AAG CCA GGA AAG GCT CCA AAG      192
Tyr Ser Asn Leu Ala Trp Tyr Gln Gln Lys Pro Gly Lys Ala Pro Lys
        50                  55                  60

CTG CTG ATC TAC GCC GCA ACA TAC TTA GCA GAT GGT GTG CCA AGC AGA      240
Leu Leu Ile Tyr Ala Ala Thr Tyr Leu Ala Asp Gly Val Pro Ser Arg
65                  70                  75                  80
```

```
TTC AGC GGT AGC GGT AGC GGT ACC GAC TTC ACC TTC ACC ATC AGC AGC      288
Phe Ser Gly Ser Gly Ser Gly Thr Asp Phe Thr Phe Thr Ile Ser Ser
                85                  90                  95

CTC CAG CCA GAG GAC ATC GCT ACC TAC TAC TGC CAA CAT TTT TGG GGT      336
Leu Gln Pro Glu Asp Ile Ala Thr Tyr Tyr Cys Gln His Phe Trp Gly
            100                 105                 110

ACT CCT CCG TTC GGC CAA GGG ACC AAG GTG GAA ATC AAA C                376
Thr Pro Pro Phe Gly Gln Gly Thr Lys Val Glu Ile Lys
        115                 120                 125
```

(2) INFORMATION FOR SEQ ID NO:55:

(i) SEQUENCE CHARACTERISTICS:
        (A) LENGTH: 125 amino acids
        (B) TYPE: amino acid
        (D) TOPOLOGY: linear (ii) MOLECULE TYPE: protein (xi) SEQUENCE DESCRIPTION: SEQ ID NO:55:

```
Met Gly Trp Ser Cys Ile Ile Leu Phe Leu Val Ala Thr Ala Thr Gly
 1               5                  10                  15

Val His Ser Asp Ile Gln Met Thr Gln Ser Pro Ser Ser Leu Ser Ala
                20                  25                  30

Ser Val Gly Asp Arg Val Thr Ile Thr Cys Arg Ala Ser Glu Asn Ile
            35                  40                  45

Tyr Ser Asn Leu Ala Trp Tyr Gln Gln Lys Pro Gly Lys Ala Pro Lys
50                  55                  60

Leu Leu Ile Tyr Ala Ala Thr Tyr Leu Ala Asp Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Gln His Phe Trp Gly
            100                 105                 110

Thr Pro Pro Phe Gly Gln Gly Thr Lys Val Glu Ile Lys
        115                 120                 125
```

(2) INFORMATION FOR SEQ ID NO:56:

(i) SEQUENCE CHARACTERISTICS:
        (A) LENGTH: 376 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..375

(ix) FEATURE:
        (A) NAME/KEY: mat_peptide
        (B) LOCATION: 1..375

(xi) SEQUENCE DESCRIPTION: SEQ ID NO:56:

```
ATG GGA TGG AGC TGT ATC ATC CTC TTC TTG GTA GCA ACA GCT ACA GGT       48
Met Gly Trp Ser Cys Ile Ile Leu Phe Leu Val Ala Thr Ala Thr Gly
 1               5                  10                  15

GTC CAC TCC GAC ATC CAG ATG ACC CAG AGC CCA AGC AGC CTG AGC GCC       96
Val His Ser Asp Ile Gln Met Thr Gln Ser Pro Ser Ser Leu Ser Ala
                20                  25                  30

AGC GTG GGT GAC AGA GTG ACC ATC ACC TGT AGA GCA AGT GAG AAT ATT      144
Ser Val Gly Asp Arg Val Thr Ile Thr Cys Arg Ala Ser Glu Asn Ile
            35                  40                  45
```

```
TAC AGT AAT TTA GCA TGG TAC CAG CAG AAG CCA GGA AAG GCT CCA AAG        192
Tyr Ser Asn Leu Ala Trp Tyr Gln Gln Lys Pro Gly Lys Ala Pro Lys
 50                  55                  60

CTG CTG ATC TAC GCC GCA ACA TAC TTA GCA GAT GGT GTG CCA AGC AGA        240
Leu Leu Ile Tyr Ala Ala Thr Tyr Leu Ala Asp Gly Val Pro Ser Arg
 65                  70                  75                  80

TTC AGC GGT AGC GGT AGC GGT ACC GAC TAC ACC TTC ACC ATC AGC AGC        288
Phe Ser Gly Ser Gly Ser Gly Thr Asp Tyr Thr Phe Thr Ile Ser Ser
                 85                  90                  95

CTC CAG CCA GAG GAC ATC GCT ACC TAC TAC TGC CAA CAT TTT TGG GGT        336
Leu Gln Pro Glu Asp Ile Ala Thr Tyr Tyr Cys Gln His Phe Trp Gly
            100                 105                 110

ACT CCT CCG TTC GGC CAA GGG ACC AAG GTG GAA ATC AAA C                  376
Thr Pro Pro Phe Gly Gln Gly Thr Lys Val Glu Ile Lys
        115                 120                 125

(2) INFORMATION FOR SEQ ID NO:57:

(i) SEQUENCE CHARACTERISTICS:
        (A) LENGTH: 125 amino acids
        (B) TYPE: amino acid
        (D) TOPOLOGY: linear (ii) MOLECULE TYPE: protein (xi) SEQUENCE DESCRIPTION: SEQ ID NO:57:

Met Gly Trp Ser Cys Ile Ile Leu Phe Leu Val Ala Thr Ala Thr Gly
 1               5                  10                  15

Val His Ser Asp Ile Gln Met Thr Gln Ser Pro Ser Ser Leu Ser Ala
                 20                  25                  30

Ser Val Gly Asp Arg Val Thr Ile Thr Cys Arg Ala Ser Glu Asn Ile
             35                  40                  45

Tyr Ser Asn Leu Ala Trp Tyr Gln Gln Lys Pro Gly Lys Ala Pro Lys
 50                  55                  60

Leu Leu Ile Tyr Ala Ala Thr Tyr Leu Ala Asp Gly Val Pro Ser Arg
 65                  70                  75                  80

Phe Ser Gly Ser Gly Ser Gly Thr Asp Tyr Thr Phe Thr Ile Ser Ser
                 85                  90                  95

Leu Gln Pro Glu Asp Ile Ala Thr Tyr Tyr Cys Gln His Phe Trp Gly
            100                 105                 110

Thr Pro Pro Phe Gly Gln Gly Thr Lys Val Glu Ile Lys
        115                 120                 125

(2) INFORMATION FOR SEQ ID NO:58:

(i) SEQUENCE CHARACTERISTICS:
        (A) LENGTH: 418 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..417

(ix) FEATURE:
        (A) NAME/KEY: mat_peptide
        (B) LOCATION: 1..417

(xi) SEQUENCE DESCRIPTION: SEQ ID NO:58:

ATG GAC TGG ACC TGG AGG GTC TTC TTC TTG CTG GCT GTA GCT CCA CGT         48
Met Asp Trp Thr Trp Arg Val Phe Phe Leu Leu Ala Val Ala Pro Arg
 1               5                  10                  15
```

```
GCT CAC TCC CAA GTG ACT CTG AGG GAG TCT GGA CCT GCC CTT GTG AGA        96
Ala His Ser Gln Val Thr Leu Arg Glu Ser Gly Pro Ala Leu Val Arg
        20                  25                  30

CCT ACA CAG ACT CTG ACA CTC ACC TGC ACC TTC TCT GGC TTC TCA TTA       144
Pro Thr Gln Thr Leu Thr Leu Thr Cys Thr Phe Ser Gly Phe Ser Leu
        35                  40                  45

AGT ACT TCT GGT ATG ACC GTA GGC TGG ATT CGC CAA CCT CCT GGA GAG       192
Ser Thr Ser Gly Met Thr Val Gly Trp Ile Arg Gln Pro Pro Gly Glu
 50                  55                  60

GCA CTG GAG TGG CTG GCA CAC ATT TGG TGG AAT GAT GAT AAG TAC TAT       240
Ala Leu Glu Trp Leu Ala His Ile Trp Trp Asn Asp Asp Lys Tyr Tyr
 65                  70                  75                  80

AAC CCT GCC CTG AAA GGC CGA CTG GCC GTC TCC AAA GAC ACA TCC AAG       288
Asn Pro Ala Leu Lys Gly Arg Leu Ala Val Ser Lys Asp Thr Ser Lys
            85                  90                  95

AAC CAG GTT GTC CTG TCC ATG AAC ACC GTG GGT CCC GGG GAC ACA GCC       336
Asn Gln Val Val Leu Ser Met Asn Thr Val Gly Pro Gly Asp Thr Ala
            100                 105                 110

ACA TAT TAC TGT GCA AGA ATG GAG GAT TAC GAC GAA GCT ATG GAC TAC       384
Thr Tyr Tyr Cys Ala Arg Met Glu Asp Tyr Asp Glu Ala Met Asp Tyr
        115                 120                 125

TGG GGC CAA GGG ATT CTG GTC ACC GTC TCC TCA G                         418
Trp Gly Gln Gly Ile Leu Val Thr Val Ser Ser
    130                 135

(2) INFORMATION FOR SEQ ID NO:59:

(i) SEQUENCE CHARACTERISTICS:
        (A) LENGTH: 139 amino acids
        (B) TYPE: amino acid
        (D) TOPOLOGY: linear (ii) MOLECULE TYPE: protein (xi) SEQUENCE DESCRIPTION: SEQ ID NO:59:

Met Asp Trp Thr Trp Arg Val Phe Phe Leu Leu Ala Val Ala Pro Arg
 1               5                  10                  15

Ala His Ser Gln Val Thr Leu Arg Glu Ser Gly Pro Ala Leu Val Arg
        20                  25                  30

Pro Thr Gln Thr Leu Thr Leu Thr Cys Thr Phe Ser Gly Phe Ser Leu
        35                  40                  45

Ser Thr Ser Gly Met Thr Val Gly Trp Ile Arg Gln Pro Pro Gly Glu
 50                  55                  60

Ala Leu Glu Trp Leu Ala His Ile Trp Trp Asn Asp Asp Lys Tyr Tyr
 65                  70                  75                  80

Asn Pro Ala Leu Lys Gly Arg Leu Ala Val Ser Lys Asp Thr Ser Lys
            85                  90                  95

Asn Gln Val Val Leu Ser Met Asn Thr Val Gly Pro Gly Asp Thr Ala
            100                 105                 110

Thr Tyr Tyr Cys Ala Arg Met Glu Asp Tyr Asp Glu Ala Met Asp Tyr
        115                 120                 125

Trp Gly Gln Gly Ile Leu Val Thr Val Ser Ser
    130                 135

(2) INFORMATION FOR SEQ ID NO:60:

(i) SEQUENCE CHARACTERISTICS:
        (A) LENGTH: 418 base pairs
        (B) TYPE: nucleic acid
        (C) STRANDEDNESS: single
        (D) TOPOLOGY: linear
```

(ix) FEATURE:
            (A) NAME/KEY: CDS
            (B) LOCATION: 1..417

(ix) FEATURE:
            (A) NAME/KEY: mat_peptide
            (B) LOCATION: 1..417

(xi) SEQUENCE DESCRIPTION: SEQ ID NO:60:

ATG GAC TGG ACC TGG AGG GTC TTC TTC TTG CTG GCT GTA GCT CCA CGT        48
Met Asp Trp Thr Trp Arg Val Phe Phe Leu Leu Ala Val Ala Pro Arg
 1               5                  10                  15

GCT CAC TCC CAA GTG ACT CTG AGG GAG TCT GGA CCT GCC CTT GTG AGA        96
Ala His Ser Gln Val Thr Leu Arg Glu Ser Gly Pro Ala Leu Val Arg
                 20                  25                  30

CCT ACA CAG ACT CTG ACA CTC ACC TGC ACC TTC TCT GGC TTC TCA TTA       144
Pro Thr Gln Thr Leu Thr Leu Thr Cys Thr Phe Ser Gly Phe Ser Leu
             35                  40                  45

AAT ACT TCT GGT ATG ACC GTA GGC TGG ATT CGC CAA CCT CCT GGA GAG       192
Asn Thr Ser Gly Met Thr Val Gly Trp Ile Arg Gln Pro Pro Gly Glu
         50                  55                  60

GCA CTG GAG TGG CTG GCA CAC ATT TGG TGG AAT GAT GAT AAG TAC TAT       240
Ala Leu Glu Trp Leu Ala His Ile Trp Trp Asn Asp Asp Lys Tyr Tyr
 65                  70                  75                  80

AAC CCT GCC CTG AAA GGC CGA CTG GCC GTC TCC AAA GAC ACA TCC AAG       288
Asn Pro Ala Leu Lys Gly Arg Leu Ala Val Ser Lys Asp Thr Ser Lys
                 85                  90                  95

AAC CAG GTT GTC CTG TCC ATG AAC ACC GTG GGT CCC GGG GAC ACA GCC       336
Asn Gln Val Val Leu Ser Met Asn Thr Val Gly Pro Gly Asp Thr Ala
                100                 105                 110

ACA TAT TAC TGT GCA AGA ATG GAG GAT TAC GAC GAA GCT ATG GAC TAC       384
Thr Tyr Tyr Cys Ala Arg Met Glu Asp Tyr Asp Glu Ala Met Asp Tyr
             115                 120                 125

TGG GGC CAA GGG ATT CTG GTC ACC GTC TCC TCA G                         418
Trp Gly Gln Gly Ile Leu Val Thr Val Ser Ser
         130                 135

(2) INFORMATION FOR SEQ ID NO:61:

(i) SEQUENCE CHARACTERISTICS:
        (A) LENGTH: 139 amino acids
        (B) TYPE: amino acid
        (D) TOPOLOGY: linear (ii) MOLECULE TYPE: protein (xi) SEQUENCE DESCRIPTION: SEQ ID NO:61:

Met Asp Trp Thr Trp Arg Val Phe Phe Leu Leu Ala Val Ala Pro Arg
 1               5                  10                  15

Ala His Ser Gln Val Thr Leu Arg Glu Ser Gly Pro Ala Leu Val Arg
                 20                  25                  30

Pro Thr Gln Thr Leu Thr Leu Thr Cys Thr Phe Ser Gly Phe Ser Leu
             35                  40                  45

Asn Thr Ser Gly Met Thr Val Gly Trp Ile Arg Gln Pro Pro Gly Glu
         50                  55                  60

Ala Leu Glu Trp Leu Ala His Ile Trp Trp Asn Asp Asp Lys Tyr Tyr
 65                  70                  75                  80

Asn Pro Ala Leu Lys Gly Arg Leu Ala Val Ser Lys Asp Thr Ser Lys
                 85                  90                  95

Asn Gln Val Val Leu Ser Met Asn Thr Val Gly Pro Gly Asp Thr Ala
                100                 105                 110

```
Thr Tyr Tyr Cys Ala Arg Met Glu Asp Tyr Asp Glu Ala Met Asp Tyr
        115                 120                 125
Trp Gly Gln Gly Ile Leu Val Thr Val Ser Ser
    130                 135
```

(2) INFORMATION FOR SEQ ID NO:62:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:62:

```
Arg Ala Ser Glu Asn Ile Tyr Ser Asn Leu Ala
1               5                   10
```

(2) INFORMATION FOR SEQ ID NO:63:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:63:

```
Ala Ala Thr Tyr Leu Ala Asp
1               5
```

(2) INFORMATION FOR SEQ ID NO:64:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:64:

```
Gln His Phe Trp Gly Thr Pro Pro
1               5
```

(2) INFORMATION FOR SEQ ID NO:65:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:65:

```
Asp Ile Gln Met Thr Gln Ser Pro Ser Ser Leu Ser Ala Ser Val Gly
1               5                   10                  15
Asp Arg Val Thr Ile Thr Cys
            20
```

(2) INFORMATION FOR SEQ ID NO:66:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:66:

```
Trp Tyr Gln Gln Lys Pro Gly Lys Ala Pro Lys Leu Leu Ile Tyr
1               5                   10                  15
```

(2) INFORMATION FOR SEQ ID NO:67:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO:67:

```
Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30
```

(2) INFORMATION FOR SEQ ID NO:68:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:68:

```
Phe Gly Gln Gly Thr Lys Val Glu Ile Lys
1               5                   10
```

(2) INFORMATION FOR SEQ ID NO:69:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:69:

```
Asp Ile Gln Met Thr Gln Ser Pro Ser Ser Leu Ser Ala Ser Val Gly
1               5                   10                  15

Asp Arg Val Thr Ile Thr Cys
            20
```

(2) INFORMATION FOR SEQ ID NO:70:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:70:

```
Trp Tyr Gln Gln Lys Pro Gly Lys Ala Pro Lys Leu Leu Ile Tyr
1               5                   10                  15
```

(2) INFORMATION FOR SEQ ID NO:71:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO:71:

```
Gly Val Pro Ser Arg Phe Ser Gly Ser Gly Ser Gly Thr Asp Tyr Thr
1               5                   10                  15

Phe Thr Ile Ser Ser Leu Gln Pro Glu Asp Ile Ala Thr Tyr Tyr Cys
            20                  25                  30
```

(2) INFORMATION FOR SEQ ID NO:72:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:72:

Phe Gly Gln Gly Thr Lys Val Glu Ile Lys
1               5                   10

(2) INFORMATION FOR SEQ ID NO:73:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:73:

Thr Ser Gly Met Thr Val Gly
1               5

(2) INFORMATION FOR SEQ ID NO:74:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:74:

His Ile Trp Trp Asn Asp Asp Lys Tyr Tyr Asn Pro Ala Leu Lys Gly
1               5                   10                  15

(2) INFORMATION FOR SEQ ID NO:75:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:75:

Met Glu Asp Tyr Asp Glu Ala Met Asp Tyr
1               5                   10

(2) INFORMATION FOR SEQ ID NO:76:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO:76:

Gln Val Thr Leu Arg Glu Ser Gly Pro Ala Leu Val Arg Pro Thr Gln
1               5                   10                  15
Thr Leu Thr Leu Thr Cys Thr Phe Ser Gly Phe Ser Leu Ser
            20                  25                  30

(2) INFORMATION FOR SEQ ID NO:77:

(i) SEQUENCE CHARACTERISTICS:
        (A) LENGTH: 14 amino acids

-continued

```
           (B) TYPE: amino acid
           (C) STRANDEDNESS: single
           (D) TOPOLOGY: linear (xi) SEQUENCE DESCRIPTION: SEQ ID NO:77:

Trp Ile Arg Gln Pro Pro Gly Glu Ala Leu Glu Trp Leu Ala
1               5                  10

(2) INFORMATION FOR SEQ ID NO:78:

(i) SEQUENCE CHARACTERISTICS:
           (A) LENGTH: 32 amino acids
           (B) TYPE: amino acid
           (C) STRANDEDNESS: single
           (D) TOPOLOGY: linear (xi) SEQUENCE DESCRIPTION: SEQ ID NO:78:

Arg Leu Ala Val Ser Lys Asp Thr Ser Lys Asn Gln Val Val Leu Ser
1               5                  10                  15

Met Asn Thr Val Gly Pro Gly Asp Thr Ala Thr Tyr Tyr Cys Ala Arg
                20                  25                  30

(2) INFORMATION FOR SEQ ID NO:79:

(i) SEQUENCE CHARACTERISTICS:
           (A) LENGTH: 11 amino acids
           (B) TYPE: amino acid
           (C) STRANDEDNESS: single
           (D) TOPOLOGY: linear (xi) SEQUENCE DESCRIPTION: SEQ ID NO:79:

Trp Gly Gln Gly Ile Leu Val Thr Val Ser Ser
1               5                  10

(2) INFORMATION FOR SEQ ID NO:80:

(i) SEQUENCE CHARACTERISTICS:
           (A) LENGTH: 30 amino acids
           (B) TYPE: amino acid
           (C) STRANDEDNESS: single
           (D) TOPOLOGY: linear (xi) SEQUENCE DESCRIPTION: SEQ ID NO:80:

Gln Val Thr Leu Arg Glu Ser Gly Pro Ala Leu Val Arg Pro Thr Gln
1               5                  10                  15

Thr Leu Thr Leu Thr Cys Thr Phe Ser Gly Phe Ser Leu Asn
                20                  25                  30

(2) INFORMATION FOR SEQ ID NO:81:

(i) SEQUENCE CHARACTERISTICS:
           (A) LENGTH: 14 amino acids
           (B) TYPE: amino acid
           (C) STRANDEDNESS: single
           (D) TOPOLOGY: linear (xi) SEQUENCE DESCRIPTION: SEQ ID NO:81:

Trp Ile Arg Gln Pro Pro Gly Glu Ala Leu Glu Trp Leu Ala
1               5                  10

(2) INFORMATION FOR SEQ ID NO:82:

(i) SEQUENCE CHARACTERISTICS:
           (A) LENGTH: 32 amino acids
           (B) TYPE: amino acid
           (C) STRANDEDNESS: single
           (D) TOPOLOGY: linear
```

(xi) SEQUENCE DESCRIPTION: SEQ ID NO:82:

Arg Leu Ala Val Ser Lys Asp Thr Ser Lys Asn Gln Val Val Leu Ser
1               5                   10                  15

Met Asn Thr Val Gly Pro Gly Asp Thr Ala Thr Tyr Tyr Cys Ala Arg
                20                  25                  30

(2) INFORMATION FOR SEQ ID NO:83:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:83:

Trp Gly Gln Gly Ile Leu Val Thr Val Ser Ser
1               5                   10

(2) INFORMATION FOR SEQ ID NO:84:

(i) SEQUENCE CHARACTERISTICS:
        (A) LENGTH: 106 amino acids
        (B) TYPE: amino acid
        (C) STRANDEDNESS: single
        (D) TOPOLOGY: linear (xi) SEQUENCE DESCRIPTION: SEQ ID NO:84:

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
                20                  25                  30

Leu Ala Trp Tyr Gln Gln Lys Gln Gly Lys Ser Pro Gln Leu Leu Val
            35                  40                  45

Tyr Ala Ala Thr Tyr Leu Ala Asp Gly Val Pro Ser Arg Phe Ser Gly
        50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Pro
                85                  90                  95

Phe Gly Ser Gly Thr Lys Leu Glu Ile Lys
                100                 105

(2) INFORMATION FOR SEQ ID NO:85:

(i) SEQUENCE CHARACTERISTICS:
        (A) LENGTH: 80 amino acids
        (B) TYPE: amino acid
        (C) STRANDEDNESS: single
        (D) TOPOLOGY: linear (xi) SEQUENCE DESCRIPTION: SEQ ID NO:85:

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
                20                  25                  30

Pro Lys Leu Leu Ile Tyr Gly Val Pro Ser Arg Phe Ser Gly Ser Gly
            35                  40                  45

Ser Gly Thr Asp Phe Thr Phe Thr Ile Ser Ser Leu Gln Pro Glu Asp
        50                  55                  60

Ile Ala Thr Tyr Tyr Cys Phe Gly Gln Gly Thr Lys Val Glu Ile Lys (2) INFORMATION FOR SEQ ID NO:86:

(i) SEQUENCE CHARACTERISTICS:
        (A) LENGTH: 106 amino acids
        (B) TYPE: amino acid
        (C) STRANDEDNESS: single
        (D) TOPOLOGY: linear (xi) SEQUENCE DESCRIPTION: SEQ ID NO:86:

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asn Ile Tyr Ser Asn
                20                  25                  30

Leu Ala Trp Tyr Gln Gln Lys Pro Gly Lys Ala Pro Lys Leu Leu Ile
            35                  40                  45

Tyr Ala Ala Thr Tyr Leu Ala Asp Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His Phe Trp Gly Thr Pro Pro
                85                  90                  95

Phe Gly Gln Gly Thr Lys Val Glu Ile Lys
            100                 105
```

(2) INFORMATION FOR SEQ ID NO:87:

(i) SEQUENCE CHARACTERISTICS:
        (A) LENGTH: 98 amino acids
        (B) TYPE: amino acid
        (C) STRANDEDNESS: single
        (D) TOPOLOGY: linear (xi) SEQUENCE DESCRIPTION: SEQ ID NO:87:

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asn Ile Tyr Ser Asn
                20                  25                  30

Leu Ala Trp Tyr Gln Gln Lys Pro Gly Lys Ala Pro Lys Leu Leu Ile
            35                  40                  45

Tyr Ala Ala Thr Tyr Leu Ala Asp Gly Val Pro Ser Arg Phe Ser Gly
 50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Phe Gly Gln Gly Thr Lys Val Glu
                85                  90                  95

Ile Lys
```

(2) INFORMATION FOR SEQ ID NO:88:

(i) SEQUENCE CHARACTERISTICS:
        (A) LENGTH: 120 amino acids
        (B) TYPE: amino acid
        (C) STRANDEDNESS: single
        (D) TOPOLOGY: linear (xi) SEQUENCE DESCRIPTION: SEQ ID NO:88:

```
Gln Val Thr Leu Lys Glu Ser Gly Pro Gly Ile Leu Gln Pro Ser Gln
 1               5                  10                  15
```

```
Thr Leu Ser Leu Thr Cys Ser Phe Ser Gly Phe Ser Leu Asn Thr Ser
            20                  25                  30

Gly Met Thr Val Gly Trp Ile Arg Gln Pro Ser Gly Lys Gly Leu Glu
            35                  40                  45

Trp Leu Ala His Ile Trp Trp Asn Asp Asp Lys Tyr Tyr Asn Pro Ala
        50                  55                  60

Leu Lys Gly Arg Leu Thr Ile Ser Lys Asp Thr Ser Asn Asn Gln Val
65                      70                  75                  80

Phe Leu Lys Ile Ala Ser Val Val Thr Ala Asp Thr Ala Thr Tyr Tyr
                85                  90                  95

Cys Ala Arg Met Glu Asp Tyr Asp Glu Ala Met Asp Tyr Trp Gly Gln
                100                 105                 110

Gly Thr Ser Val Thr Val Ser Ser
            115                 120

(2) INFORMATION FOR SEQ ID NO:89:

(i) SEQUENCE CHARACTERISTICS:
        (A) LENGTH: 87 amino acids
        (B) TYPE: amino acid
        (C) STRANDEDNESS: single
        (D) TOPOLOGY: linear (xi) SEQUENCE DESCRIPTION: SEQ ID NO:89:

Gln Val Thr Leu Arg Glu Ser Gly Pro Ala Leu Val Arg Pro Thr Gln
1               5                   10                  15

Thr Leu Thr Leu Thr Cys Thr Phe Ser Gly Phe Ser Leu Ser Trp Ile
            20                  25                  30

Arg Gln Pro Pro Gly Glu Ala Leu Glu Trp Leu Ala Arg Leu Ala Val
            35                  40                  45

Ser Lys Asp Thr Ser Lys Asn Gln Val Val Leu Ser Met Asn Thr Val
        50                  55                  60

Gly Pro Gly Asp Thr Ala Thr Tyr Tyr Cys Ala Arg Trp Gly Gln Gly
65                  70                  75                  80

Ile Leu Val Thr Val Ser Ser
            85

(2) INFORMATION FOR SEQ ID NO:90:

(i) SEQUENCE CHARACTERISTICS:
        (A) LENGTH: 120 amino acids
        (B) TYPE: amino acid
        (C) STRANDEDNESS: single
        (D) TOPOLOGY: linear (xi) SEQUENCE DESCRIPTION: SEQ ID NO:90:

Gln Val Thr Leu Arg Glu Ser Gly Pro Ala Leu Val Arg Pro Thr Gln
1               5                   10                  15

Thr Leu Thr Leu Thr Cys Thr Phe Ser Gly Phe Ser Leu Ser Thr Ser
            20                  25                  30

Gly Met Thr Val Gly Trp Ile Arg Gln Pro Pro Gly Glu Ala Leu Glu
            35                  40                  45

Trp Leu Ala His Ile Trp Trp Asn Asp Asp Lys Tyr Tyr Asn Pro Ala
        50                  55                  60

Leu Gly Lys Arg Leu Ala Val Ser Lys Asp Thr Ser Lys Asn Gln Val
65                  70                  75                  80

Val Leu Ser Met Asn Thr Val Gly Pro Gly Asp Thr Ala Thr Tyr Tyr
                85                  90                  95
```

```
Cys Ala Arg Met Glu Asp Tyr Asp Glu Ala Met Asp Tyr Trp Gly Gln
            100                 105                 110

Gly Ile Leu Val Thr Val Ser Ser
        115             120

(2) INFORMATION FOR SEQ ID NO:91:

(i) SEQUENCE CHARACTERISTICS:
        (A) LENGTH: 120 amino acids
        (B) TYPE: amino acid
        (C) STRANDEDNESS: single
        (D) TOPOLOGY: linear (xi) SEQUENCE DESCRIPTION: SEQ ID NO:91:

Gln Val Thr Leu Arg Glu Ser Gly Pro Ala Leu Val Arg Pro Thr Gln
1               5                   10                  15

Thr Leu Thr Leu Thr Cys Thr Phe Ser Gly Phe Ser Leu Asn Thr Ser
            20                  25                  30

Gly Met Thr Val Gly Trp Ile Arg Gln Pro Pro Gly Glu Ala Leu Glu
            35                  40                  45

Trp Leu Ala His Ile Trp Trp Asn Asp Asp Lys Tyr Tyr Asn Pro Ala
    50                  55                  60

Leu Gly Lys Arg Leu Ala Val Ser Lys Asp Thr Ser Lys Asn Gln Val
65                  70                  75                  80

Val Leu Ser Met Asn Thr Val Gly Pro Gly Asp Thr Ala Thr Tyr Tyr
                85                  90                  95

Cys Ala Arg Met Glu Asp Tyr Asp Glu Ala Met Asp Tyr Trp Gly Gln
            100                 105                 110

Gly Ile Leu Val Thr Val Ser Ser
        115             120
```

RESHAPED HUMAN ANTIBODY TO HUMAN INTERLEUKIN-6

This application is a divisional application Ser. No. 08/553,501, filed Feb. 20, 1996 now U.S. Pat. No. 5,856,135, which is the national phase of PCT/JP94/00859, filed May 30, 1994.

TECHNICAL FIELD

The present invention relates to a human/mouse chimeric antibody comprising variable regions (V regions) of mouse monoclonal antibody SK2 to human interleukin-6 (IL-6) and constant regions (C regions) of human antibody; a reshaped human antibody wherein the complementarity determining regions (CDRs) of a human light chain (L chain) V region and a human heavy chain (H chain) V region are replaced with CDRs of the mouse monoclonal antibody to human IL-6 (SK2); as well as L chains and H chains comprising said antibody.

The present invention further provides DNA coding for said antibody, especially the V regions thereof. The present invention also provides vectors especially expression vectors, comprising said DNA, and hosts transformed with said vectors. The present invention further provides a process for the production of a chimeric antibody to human IL-6, and a process for the production of a reshaped human antibody to human IL-6.

BACKGROUND ART

Interleukin-6 is a multifunctional cytokine produced by a variety of cells. This cytokine controls immune response, the acute phase reaction and hematopiesis, and plays a central role in the host defense mechanisms (Kishimoto et al., Blood, 74, 1–10, 1989). This cytokin acts on various tissues, and exhibits growth induction effects, growth inhibitory effects and differentiation induction effects, depending on the nature of the target cell.

It has been suggested that an abnormal expression of the IL-6 gene is related to the generation of various diseases, particularly autoimmune disease, mesangial proliferative glomerulonephritis and plasmacytoma/myeloma (Hirano et al., Immunol. Today, 11, 443–449, 1990; Clein, B. et al., Eur. Cytokins Net. 1, 193–201, 1990). Accordingly, antibodies which inhibit the function of IL-6 are expected to be useful as therapeutic agents in human patients.

In fact, in clinical research wherein mouse monoclonal antibody to human IL-6 was used to treat terminal patients with plasmacytoma, inhibition of the growth of the plasmacytoma, as well as decreases in the levels of circulating M protein, serum calcium, serum IgG and C-reactive protein were shown (Klein, B. et al., Blood, 78, 1198–1204, 1991; Klein, B. et al., Res. Immunol., 143, 774–776, 1992).

Mouse monoclonal antibodies are highly immunogenic (in other words, "antigenic") in humans, and therefore their therapeutic value in humans is limited. In addition, although mouse monoclonal antibodies may block target activities, they cannot be administered frequently without causing an immune response which results in the danger of an undesirable allergic response.

To solve these problems, processes for the production of humanized antibodies have been developed. Mouse antibodies can be humanized by two processes. The simpler method provides a chimeric antibody comprising variable regions derived from a mouse monoclonal antibody and constant regions derived from a human antibody. The resulting chimeric antibody comprises the entire variable regions of a mouse antibody and would be expected to bind to an antigen with the same specificity as the mouse antibody.

In addition, in a chimeric antibody, the proportion of protein sequence derived from a source other than human is decreased, and therefore its immunogenicity would be expected to be lower than that of a mouse antibody. Although chimeric antibodies bind well to antigens and have a lower antigenicity, there is still a possibility that an immune response to the mouse variable regions will occur (LoBuglio et al., Proc. Natl. Acad. Sci. USA, 84, 4220–4224, 1989).

Although the second process for humanizing a mouse antibody is more complicated, it further lowers the potential immunogenicity of the mouse antibody. In this process, complementarity determining regions (CDRs) from the variable regions of a mouse antibody are transplanted into the variable regions of a human antibody to construct reshaped human antibody variable regions.

Next, these reshaped human variable regions are joined to the constant regions of a human antibody. The only portions derived from a protein sequence other than human protein sequence in the finally reshaped humanized antibody are the CDRs and minor portions of the framework regions (FRs). CDRs are composed of hypervariable protein sequences. They do not represent species-specific sequence. For these reasons, a reshaped human antibody carrying mouse CDRs should not have immunogenicity higher than that of a natural human antibody comprising human CDRs.

For reshaped human antibodies, see further Richmann, L. et al., Nature, 322, 323–327, 1988; Verhoeye, M. et al., Science, 239, 1534–1536, 1988; Kettleborough, C. A. et. al., Protein Engineering. 1, 773–783, 1991; Maeda, H. et al., Human Antibodies and Hybridoma, 2, 124–134, 1991; Gorman, S. G. et al., Proc. Natl. Acad. Sci. USA, SE, 4181–4185, 1991; Tempert, P. R. et al., Bio/Technology, 9, 266–271, 1991; Co, M. S. et al., Proc. Natl. Acad. Sci. USA, 88, 2869–2873, 1991; Carter, P. et al., Proc. Natl. Acad. Sci. USA, 89, 4285–4289, 1992; Co, M. N. et al., J. Immunol. 147, 1149–1154, 1992; and Sato, K. et al., Cancer Res. 53, 1–6, 1993.

DISCLOSURE OF INVENTION

As described above, although reshaped human antibodies are expected to be useful for therapeutic purposes, reshaped human antibodies to human IL-6 are not known. In addition, there is no process for the production of a reshaped human antibody which is universally applicable. Accordingly, various strategies are necessary to construct a reshaped human antibody sufficiently active against a particular antigen (for example, see, Sata, K. et al., Cancer Res. 53, 851–856 (1993).

The present inventors found that a mouse monoclonal antibody, SK2, to human IL-6 strongly inhibited the functions of IL-6 in an in-vivo animal test, and therefore was promising as a therapeutic agent in IL-6-related diseases (Saito, H. et al., Proc. 21st Meeting of the Japanese Society for Immunology, Abstract, 21, 116, 1991). Therefore, the present invention is intended to provide antibodies to human IL-6, having low immunogenicity.

Accordingly, the present invention relates to reshaped human antibodies derived from the mouse monoclonal antibody SK2 against human IL-6. The present invention also provides human/mouse chimeric antibodies useful in the construction of the reshaped human antibodies. The present invention further relates to genetic engineering processes for the production of reshaped human antibodies and chimeric antibodies based on the mouse monoclonal antibody SK2.

Particularly, the present invention relates to, a chimeric antibody to human IL-6, comprising:
  (1) L chains comprising human antibody L chain C regions, and L chain V regions of the mouse monoclonal antibody SK2 to human IL-6, and
  (2) H chains comprising human antibody H chain C regions, and H chain V regions of the mouse monoclonal antibody SK2 to human IL-6; as well as;

a reshaped human antibody based on the mouse monoclonal antibody SK2 to human IL-6, composed of reshaped human L chain V regions comprising
  (1) framework regions (FRs) of a human antibody L chain V region, and
  (2) CDRs of the L chain V region of the mouse monoclonal antibody SK2 to human IL-6; and
reshaped human H chain V regions, comprising
  (1) FRs of a human antibody H chain V region, and
  (2) CDRs of the H chain V region of the mouse monoclonal antibody SK2 to human IL-6.

The present invention also relates to polypeptides of the L chains and H chains forming the above-mentioned various antibodies, and DNAs coding therefor.

The present invention further relates to expression vectors comprising said DNAs, and hosts transformed with said expression vectors.

The present invention yet further relates to a process for the production of the chimeric antibodies to human IL-6, and a process for the production of the reshaped human antibodies to human IL-6.

BRIEF EXPLANATION OF DRAWINGS

FIG. 10 is a graph comparing the abilities of four reshaped human SK2 antibodies of the present invention to inhibit the binding of IL-6 to IL-6R, with that of an SK2 chimeric antibody and the mouse monoclonal antibody SK2.

Figure 1:
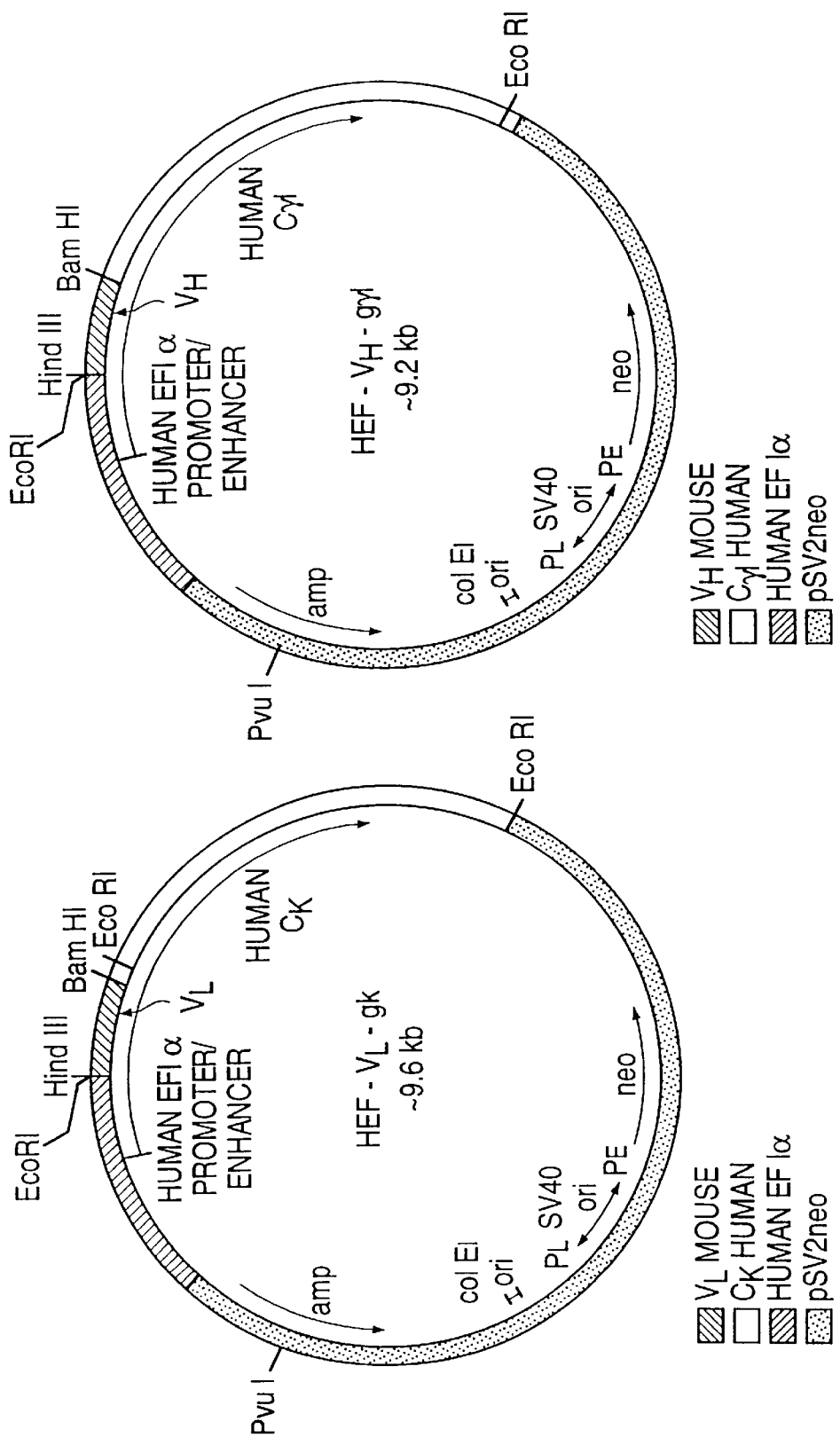
FIG. 1 shows the expression plasmids HEF-$V_L$-gk and HEF-$V_H$-gγ1 comprising the human EFI-α promoter/enhancer, useful for the expression of L chains and H chains, respectively.

Specific Embodiments for Carrying Out the Present Invention

Cloning of DNA coding for V regions of mouse antibody

DNA coding for the V regions of a mouse monoclonal antibody to human IL-6 can be cloned by preparing total RNA from cells producing a mouse monoclonal antibody, converting the RNA to single-stranded cDNA according to a known method, and amplifying desired cDNA by the polymerase chain reaction (PCR). As a source of the total RNA, a hybridoma producing a monoclonal antibody to human IL-6 must be constructed. As such, the hybridoma SK2 may be mentioned. A process for construction of the hybridoma SK2 is described hereinafter in Reference Example 1.

(1) Preparation of total RNA

In the present invention, although the total RNA was obtained by disrupting the hybridoma cells and treating them with guanidine thiocyanate followed by cesium chloride density-gradient centrifugation (Chirgwin et al., Biochemistry, 18, 5294, 1979), methods already used in the cloning of genes for other proteins, for example a method using surfactant treatment and phenol treatment in the presence of a ribonuclease inhibitor such as vanadium complex (Berger & Birkenmeier, Biochemistry, 18, 5143, 1979), may be used.

(2) Preparation of single-stranded cDNA treating the total RNA thus obtained as a template, adding as a primer an oligo (dT) complementary to the poly A sequence present at the 3'-terminus of mRNA, and treating the mixture with a reverse transcriptase to synthesize single-stranded DNA (cDNA) complementary to the total mRNA (Larrik, J. W. et al. Biotechnology, 7, 934, 1989). Alternatively, a random primer may be used.

(3) Amplification of mouse antibody V region by polymerase chain reaction (PCR)

Next, a mouse antibody V region is specifically amplified from said cDNA by the polymerase chain reaction (PCR). For such amplification of the mouse antibody V region, primers described in Jones, S. T. et al., Biotechnology, 9, 88–89, 1991 may be used. To design the primers used for cloning the mouse monoclonal antibody SK2 produced by the hybridoma SK2, the types of both the H chain and the L chain must be determined.

The SK2 antibody was typed using a mouse monoclonal antibody isotyping kit (Amersham International). As a result, it was established that the SK2 antibody has κ type L chains and γ1 type H chains. The typing of the SK2 antibody is described hereinafter in Reference Example 2.

Next, to amplify a Kappa (κ) type L chain V region of a mouse monoclonal antibody using the polymerase chain reaction (PCR), 11 oligonucleotide primers (Mouse Kappa Variable; MKV) shown in SEQ ID NOs: 1 to 11, and an oligonucleotide primer (Mouse Kappa Constant; MKC) shown in SEQ ID NO: 12 are used as 5'-terminal primers and 3'-terminal primer, respectively.

The above-mentioned MKV primers hybridize to a DNA sequence coding for the mouse kappa type L chain leader sequence, and the above-mentioned MKC primer hybridizes to a DNA sequence coding for the mouse kappa type L chain C region.

To amplify an H chain V region of a mouse monoclonal antibody, 12 oligonucleotide primers (Mouse Heavy Variable; MHV) shown in SEQ ID NOs: 13 to 24, and an oligonucleotide primer (Mouse Heavy Constant; MHC) shown in SEQ ID NO: 25 are used as 5'-terminal primers and 3'-terminal primer, respectively.

Note, in the present Examples, the 5'-terminal primers contain near their 5'-terminal the sequence GTCGAC providing a restriction enzyme SAlI cleavage site, and the 3'-terminal primers contain near their 5'-termini the nucleotide sequence CCCGGG providing a restriction enzyme XmaI cleavage site. These restriction cleavage sites so far as they can be used to subclone a desired DNA fragment coding for a variable region into a cloning vector.

Next, to obtain a DNA fragment coding for a desired variable region of a mouse monoclonal antibody, the amplification product is cleaved with the restriction enzymes SalI and XmaI, and isolated and purified by low-melting agarose gel electrophoresis or on a column (PCR product purification kit (QIAGEN), DNA purification kit (GENECLEAN II)). In a like manner, appropriate cloning vectors such as plasmid pUC19, are cleaved with the same restriction enzymes, SalI and XmaI, and the above-mentioned DNA fragment is ligated to the cleaved pUC19 to obtain a plasmid containing a DNA fragment coding for the desired variable region of the mouse monoclonal antibody.

The cloned DNA can be sequenced by any conventional procedure, for example, using Sequenase Version 2.0 (United States Biochemical Corporation).

The cloning and sequencing of desired DNA are described specifically in Examples 1 and 2.

Complementarity Determining Regions (CDRs)

The V regions of the L chains and the H chains form an antigen-binding site. The variable regions on the L chains and the H chains are formed from the linkage of four relatively conserved framework regions and three hypervariable or complementarity determining regions (CDRs) having common properties (Kabat, E. A. et al., "Sequences of Proteins of Immunological Interest", US Dept. Health and Human Services, 1983).

A major portion of each of the above-mentioned four framework regions (FRs) forms a β-sheet structure, and as a result the three CDRs form loops. In some cases, the CDRs may form a part of the β-sheet. The three CDRs are maintained in positions sterically close to each other by the FRs, and are responsible for the paired formation of an antigen-binding site together with the three paired CDRs.

Three CDRs can be identified according to an empirical rule of Kabat, E. A. et al., "Sequences of Proteins of Immunological Interest", by comparing the amino acid sequence of the V region of an antibody obtained and the known amino acid sequence of the V region of a known antibody, as specifically explained in Example 3.

Construction of Chimeric Antibody

Prior to designing a reshaped human V region of an antibody to human IL-6, it was necessary to confirm that the CDRs to be used actually formed an antigen-binding region. For this purpose, a chimeric antibody was constructed. In addition, the amino acid sequence of a mouse anti-human IL-6 antibody deduced from the nucleotide sequence of a cloned DNA for the monoclonal antibody SK2, was compared with that of the V regions of known mouse and human antibodies.

Once DNA fragments coding for the L chain and H chain V regions of the mouse monoclonal antibody SK2 are cloned, these mouse V regions are joined with DNAs coding for human antibody constant regions, and expressed to obtain a chimeric anti-human IL-6 antibody.

A basic process for the construction of a chimeric antibody comprises joining a mouse leader sequence and V region sequence present in a cloned cDNA to a sequence coding for a human antibody C region present in an eukaryotic expression vector.

The human antibody C regions may be any human L chain C region and any human H chain C region, such as human L chain Cκ and H chain Cγ1 or Cγ4.

For the production of a chimeric antibody, tow expression vectors are constructed, i.e., an expression vector comprising a DNA coding for a mouse L chain V region and a human L chain C region under the control of an expression control region such as an enhancer/promoter system; and an expression vector comprising a DNA coding for a mouse H chain V region and a human H chain C region under the control of an expression control region such as an enhancer/promoter region. Next, these expression vectors are used to cotransfect host cells such as mammalian cells, and the transformed cells are cultured in-vitro or in-vivo to produce a chimeric antibody (for example, see, WO 91-16928).

Alternatively, a DNA coding for a mouse L chain V region and a human L chain C region, and a DNA coding for a mouse H chain V region and a human H chain C region are introduced into a single expression vector, which vector is used to transform host cells, and these transformed cells are then cultured in vivo or in vitro to produce a desired chimeric antibody.

Construction of a chimeric antibody is described in Example 4.

A cDNA coding for a mouse SK2 κ type L chain leader region and a V region is subcloned using the PCR method, and joined to an expression vector containing a genomic DNA coding for a human L chain Cκ region. A cDNA coding for the mouse SK2 antibody γ1 type H chain leader region and V region is subcloned using the PCR method, and joined to an expression vector containing a genomic DNA coding for a human H chain Cγ1 region.

Using specifically designed PCR primers, appropriate nucleotide sequences are introduced into the 5'-and 3'-terminal portions of cDNAs coding for the V regions of mouse SK2 antibody so that the cDNA can easily be inserted into an expression vector and the expression can adequately function (for example, in the present invention, the expression vector is devised so as to increase the transcription efficiency by introducing a Kozak sequence). Next, the V regions of the mouse SK2 antibody amplified by PCR using the above-mentioned primers are inserted into HEF expression vectors containing desired human C regions (FIG. 1). These vectors are suitable for transient expression or stable expression of a genetically engineered antibody in various mammalian cell lines.

In addition to the chimeric SK2 antibody having V regions the same as those present in the mouse SK2 antibody, a second version (NTS) of chimeric SK2 antibody was constructed. In the chimeric SK2 antibody NTS, the 30th amino acid, asparagine, in the H chain V region has been changed to serine.

In mouse H chain V regions belonging to mouse H chain subgroup I (Fischmann, T. O. et al., J. Biol. Chem. 266, 12915, 1991), the most typical 30th position similarly to the native SK2 antibody, the mutant chimeric SK2 antibody NTS does not have a glycosylation site.

The chimeric SK2 antibody exhibited binding activity against human IL-6. The chimeric SK2 antibody NTS bound to human IL-6, too. Therefore, it was shown that the correct mouse V region had been cloned and sequenced. In addition, it was shown that glycoaylation of the H chain V region of the SK2 antibody is not necessary for binding activity of the SK2 antibody.

Construction of Reshaped Human Antibody

To construct a reshaped human antibody wherein the CDRs of a mouse monoclonal antibody have been transplanted into a human antibody, it is desirable that homology exists between the FRs of the mouse monoclonal antibody and the FRs of the human antibody. Therefore, the V regions of the L chain and the H chain of the mouse SK2 antibody were compared with the V regions of all known antibodies whose structure was known, using the Protein Data Bank. The result is summarized in Table 1.

TABLE 1

Homology (%) between V regions of mouse SK2 antibody and consensus sequences of human V regions of various subgroups

|  | HSGI | HSGII | HSGIII | HSGIV |
|---|---|---|---|---|
| A. L chain V region |  |  |  |  |
| SK2 | 60.3% | 51.3% | 56.0% | 56.6% |
| B. H chain V region |  |  |  |  |
| SK2 | 36.2% | 59.2% | 44.7% |  |

The L chain V region of the mouse antibody SK2 is most similar to the consensus sequence of subgroup I (HSGI) of human L chain V regions, there being a homology of 60.3%. The H chain V region of the mouse antibody SK2 is most similar to subgroup II(HSGII) of human H chain V regions, there being a homology of 59.2%.

From a comparison of the V regions in human antibodies, it is possible to select FRs of human V regions which are used as a base for designing the V regions of a reshaped human SK2 antibody. A human L chain V region belonging to subgroup I (SGI) is preferably used for designing an L chain V region of a reshaped human SK2 antibody, and a human H chain V region belonging to subgroup II (SGII) is preferably used for designing an H chain V region of a reshaped human SK2 antibody. In addition, it may be best to select a region having a homology as high as possible (Kabat, E. A. et al., US Dept. Health and Human Services, US Government Printing Offices, 1991).

Design of V region of reshaped human SK2 antibody

The first step in the design of the V regions of a reshaped human SK2 antibody was the selection of human antibody V regions used as the basis of design. The L chain V region of the mouse SK2 antibody was most similar to human κ type antibody L chain V regions belonging to subgroup I (Table I). In a comparison with the L chain V regions of known human antibodies, the L chain V region of the mouse SK2 antibody showed 63% homology to the human L chain V region REI which is a member of subgroup I. Accordingly, FRs of REI were used as a starting material for construction of the L chain V region of reshaped human SK2 antibody.

Two versions of L chain V region of reshaped human SK2 antibody were designed. In the first version (version "a"), the human FRs were the same as FRs based on REI present in the reshaped human CAMPATH-1H antibody (Riechmann, l. et al., Mature 322, 21–25, 1988) (version "a" of L chain V region of reshaped human PM-1 described in WO92-19759), and the mouse CDRs were the same as CDRs in the L chain V region of the mouse SK2 antibody. The second version (version "b") is different from the version "a" in one amino acid at position 71 in the human FR3.

Namely, in the FRs of the modified REI used for designing version "a", position 71 in phenylalanine, while in version "b", the phenylalanine at position 71 has been changed to tyrosine, as found in the L chain V region of the mouse SK2 antibody. Table 2 shows the amino acid sequences of the L chain V regions of the mouse SK2 antibody, the FRs of REI, as well as two versions of the L chain V region of reshaped human SK2 antibody.

TABLE 2

```
                      FR1                        CDR1

1         2               3
                 12345678901234567890123   45678901234

VLSK2   DIQMTQSPASLSVSVGETVTITC   RASENIYSNLA    (SEQ ID NO:84)
         REI     DIQMTQSPSSLSASVGDRVTITC                  (SEQ ID NO:85)
         RVLa    DIQMTQSPSSLSASVGDRVTITC   RASENIY5NLA    (SEQ ID NO:86)
         RVLb    -----------------------   -----------    (SEQ ID NO:87)

FR2              CDR2

4            5
                 567890123456789  0123456

VLSK2   WYQQKQGKSPQLLVY  AATYLAD
         REI     WYQQKPGKAPKLLIY
         RVLa    WYQQKPGKAPKLLIY  AATYLAD
         RVLb    ---------------  -------

FR3                           CDR3
                  6        7         8                 9
                  769012345679901234567890123456 78    901234567

VLSK2    GVPSRYSGSGSGTQYSLKINSLQSEDFGSYYC     QHFWGTPP-
         REI      GVPSRFSGSGSGTDFTFTISSLQPEDIATYYC
         RVLa     GVPSRPSGSGSGTDFTFTISSLQPEDZATYYC     QRFWGTPP-
         RVLb     --------------Y-----------------

FR4

1
                  0
                  8901234567
```

TABLE 2-continued

| | |
|---|---|
| VLSK2 | FGSGTKLEIK |
| REI | FGQGTKVEIK |
| RVLA | FGQGTKVEIK |
| RVLb | ---------- |

Note: Five underlined amino acids in the FRs of REI show the positions of amino acids differently from those in the human REI amino acid sequence (Palm, W. et al., Hoppe-Seyler's, Z. Physiol. Chem., 356, 167–191, 1975).

The FRs in the H chain V region of the mouse SK2 antibody are most similar to those in human H chain V regions belonging to subgroup II (Table I). In a comparison with known human antibody H chain V regions, the H chain V region of the mouse SK2 antibody was very similar (60.8% homology) to the human H chain V region DAW (Press, E. M. et al., Biochem. J. 117, 641, 1970), which is a member of subgroup II of human H chain V regions. In addition, the sizes of the CDRs were very close between the mouse SK2 antibody and the human antibody DAW. For this reason, FRs of the human antibody DAW were used as starting material for construction of the H chain V region of reshaped human SK2 antibody.

Two versions of the H chain V region of reshaped human SK2 antibody were designed. In version "a", the FRs were the same as those of DAW, and in version "b", only the 30th position in human FR1 was different. Namely, in version "a", the amino acid at position 30 was serine, while in version "b", the amino acid at position 30 was asparagine.

Table 3 shows the amino acid sequences of the H chain V regions of the mouse SK2 antibody, the FRs of DAW, as well as the versions "a", and "b" of the H chain V region of reshaped SK2 antibody.

Reshaped human SK2 antibody of the present invention comprises:
(A) L chains comprising
  (1) a human L chain C region, and
  (2) an L chain V region comprising human L chain FRs, and L chain V region CDRs of the mouse monoclonal antibody SK2 to human IL-6; and
(B) H chains comprising
  (1) a human H chain C region, and
  (2) an H chain V region comprising human H chain FRs, and H chain V region CDRs of the mouse monoclonal antibody SK2 to human IL-6.

In a preferred embodiment, the above-mentioned L chain V region has the amino acid sequence shown in SEQ ID NO: 55 or 57, and the above-mentioned H chain V region has the amino acid sequence shown in SEQ ID NO: 59 or 61. The above-mentioned human L chain C region may be any human L chain C region such as a human κ C region; and the above-mentioned human H chain C region may be any human H chain C region such as a human Cγ1 region, human Cγ4 region etc.

For the production of a reshaped human antibody, two expression vectors are constructed, i.e., an expression vector comprising a DNA coding for the above-defined reshaped human antibody L chain under the control of an expression control region such as an enhancer/promoter system, and an another expression vector comprising a DNA coding for the

TABLE 3

| | FR1 | CDR1 | FR2 | |
|---|---|---|---|---|
| | 1         2         3<br>12345678901234567890123456789 0 | 1234555<br>AB | 4<br>67890123456789 | |
| VHSK2 | QVTLKESGPGILQPSQTLSLTCSFSGFSLN | TSGMTVG | WIRQPSGKGLEWLA | (SEQ ID NO:88) |
| DAW | QVTLRESGPALVRPTQTLTLTCSFSGFSLN | | WIRQPPGEALEWLA | (SEQ ID NO:89) |
| RVHa | QVTLRESGPALVRPTQTLTLTCSFSGFSLN | TSGMTVG | WIRQPPGEALEWLA | (SEQ ID NO:90) |
| RVHb | ----------------------------N | ------- | -------------- | (SEQ ID NO:91) |

| | CDR2 | FR3 |
|---|---|---|
| | 5         6         7         8         9<br>0123456789012345 67890123456789012222345678901234<br>ABC | |
| VHSK2 | HIWWNDDKYYNPALKG | RLTISKLTSNNQVPLKIASVVTADTATYYCAR |
| DAW | | RLAVSKDTSKNQVVLSMNTVGPGDTATYYCAR |
| RVHa | HIWWNDDKYYNPALKG | RLAVSKDTSKNQVVLSMNTVGPGDTATYYCAR |
| RVHb | ---------------- | -------------------------------- |

| | CDR3 | FR4 |
|---|---|---|
| | 1<br>0         1<br>5678900012<br>AB | 34567890123 |
| VHSK2 | MEDYDEAMDY | WGQGTSVTVSS |
| DAW | | WGQGILVTVSS |
| RVHa | MEDYDEAMDY | WGQGILVTVSS |
| RVHb | ---------- | ----------- |

Construction of reshaped human SK2 antibody

The construction of reshaped human SK antibody V regions is described in detail in Example 5.

above-defined reshaped human H chain under the control of an expression control region such as an enhancer/promoter system. Next, these expression vectors are used to co-transfect host cells, such as mammalian cells, and transformed cells are cultured in vivo or in vitro to produce a reshaped human antibody (see, for example, WO91-16927).

Alternatively, a DNA coding for a reshaped human L chain and a DNA coding for a reshaped human H chain are introduced into a single expression vector which is used to transfect host cells, and the transformed host cells are then cultured in vivo or in vitro to produce a desired reshaped human antibody.

As described above, a transformant with genes coding for a desired chimeric antibody or reshaped human antibody is cultured, and the produced chimeric antibody or reshaped human antibody may be separated from the inside of the cells or the outside of the cells, and purified to homogeneity.

Note, the present desired protein, i.e., a chimeric antibody or a reshaped human antibody, may be isolated and purified using a protein A agarose column. In addition, other procedures used for the isolation and purification of proteins may be used, without any limitations. For example, various chromatographic procedures, ultrafiltration, salting out, dialysis, etc. may be used alone or in combination to isolate or purify a chimeric antibody or a reshaped human antibody.

For the production of the present chimeric antibodies or reshaped human antibodies to human IL-6, any expression system, such as eukaryotic cells, for example animal cells, such as established mammalian cells, fungal cells and yeast cells, as well as prokaryotic cells, for example bacterial cells such as E. coli, may be used. Preferably, the present chimeric antibodies or reshaped human antibodies are expressed in mammalian cells, such as COS cells or CHO cells.

Figure 2:
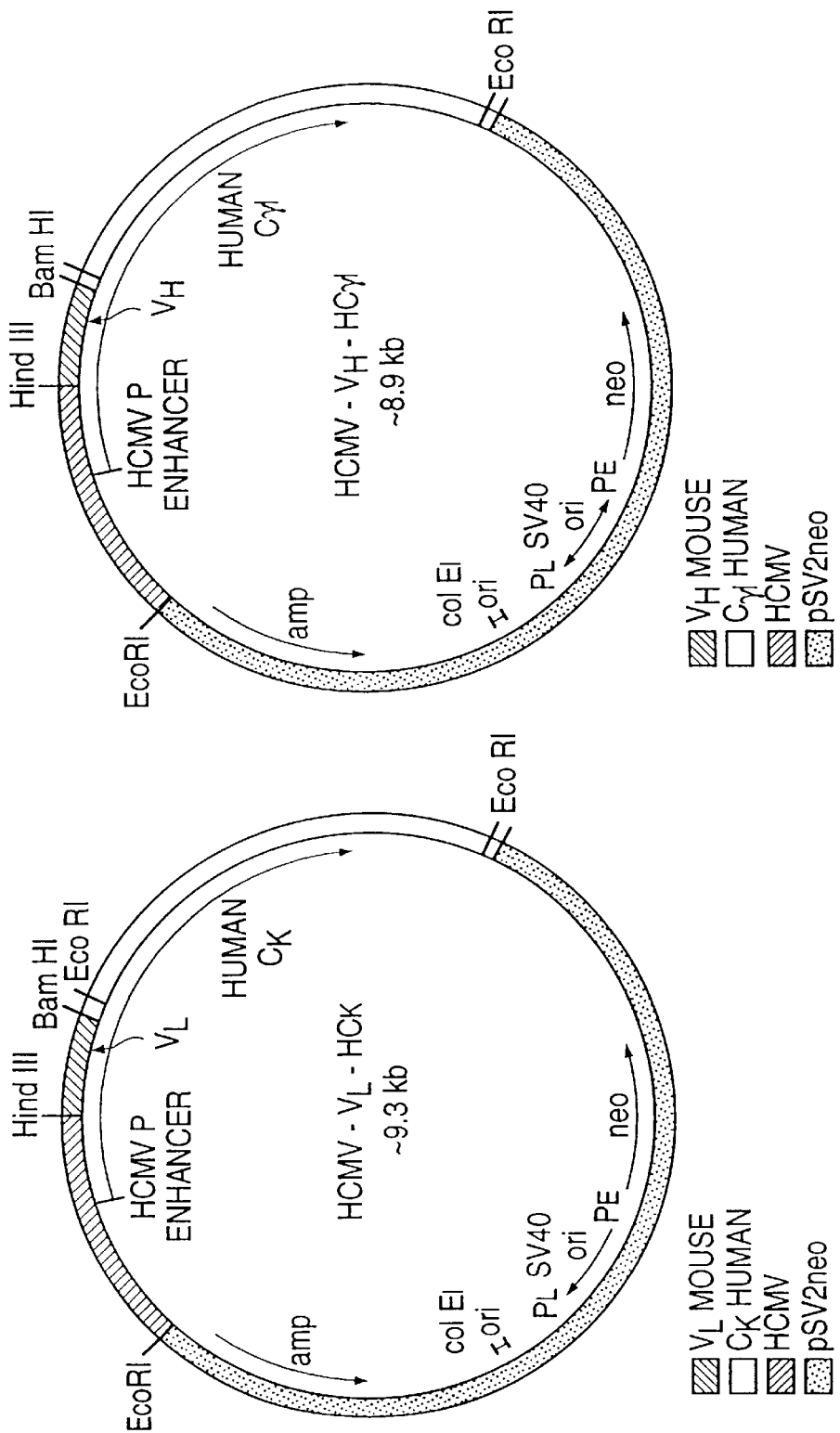
FIG. 2 shows expression vectors comprising the human cytomegalovirus (HCMV) promoter/enhancer, useful for the expression of the present antibody peptides.

In these cases, conventional promoters useful for expression in mammalian cells can be used. For example, a human cytomegalovirus immediate early (HCMV) promoter is preferably used. Examples of expression vectors comprising the HCMV promoter include HCMV-$V_H$-HCγ1, HCMV-$V_L$-HC$_κ$ etc. derived from pSV2neo (see FIG. 2) (WO92-19759).

In addition, viral promoters derived from retroviruses, polyoma virus, adenoviruses, simian virus 40 etc. as well as promoters derived from mammalian cells such as human polypeptide chain elongation factor (HEF-1α) gene promoter can be used as promoters for gene expression in mammalian cells useful for the present invention. For example, an SV40 promoter can be used according to the method of Mulligan et. al., Nature 277, 108 (1979); and HEP-1α promoter can easily be used according to the method of Mizushima, s. et al., Nucleic Acids Res., 18, 5322, 1990.

As origins of replication, those derived from SV40, polyoma virus, adenoviruses, bovine papilloma virus (BPV), etc., can be used. In addition, to amplify gene copies in host cells, an expression vector may contain, as a selection marker, the phosphotransferase APH (3')II or I (neo) gene, the thymidine kinase (TK) gene, the E. coli xanthine-quanidine phosphoribosyltransferase (Ecogpt) gene, the dihydrofolate reductase (DHFR) gene or the like.

EXAMPLES

Next, the present invention is explained more thoroughly in the following Examples, though the scope of the present invention should not be limited thereto.

Example 1 Cloning of DNA coding for V regions of mouse monoclonal antibody to human IL-6

DNA coding for the V regions of a mouse monoclonal antibody, SK2, to human IL-6 was cloned as follows.

1. Preparation of total RNA

Total RNA from a hybridoma, SK2, was prepared according to procedures described in Chirgwin et al., Biochemistry, 18, 5294 (1979). Namely, cells of the hybridoma SK2 were completely homogenized in 20 ml of 4 M guanidine thiocyanate (Fluka). The homogenate was overlaid on 5.3 M cesium chloride solution in a centrifuge tube, which was then centrifuged in a Beckman SW40 rotor at 31,000 rpm and 20° C. for 24 hours to precipitate the RNA.

The RNA precipitate was washed with 80% ethanol, dissolved in 150 μl of 10 mM Tris-HCl (pH 7.5) containing 1 mM EDTA and 0.5% SDS, and after adding Proteinase (Boehringer) to a concentration of 0.5 mg/ml, the mixture was incubated at 37° C. for 20 minutes. The mixture was extracted with phenol and chloroform, and RNA was precipitated with ethanol. Next, the RNA precipitate was dissolved in 200 μl of 10 mM Tris-HCl (pH 7.5) containing 1 mM EDTA.

2. Synthesis of single-stranded cDNA

To synthesize single-stranded cDNA according to the procedure described in J. W. Larrick et al., Biotechnology, 7, 934 (1989), about 5 μg of the total RNA prepared as described above was dissolved in 10 μl of 50 mM Tris-HCl buffer (pH 8.3) containing 40 mM KCl, 6 mM $MgCl_2$, 10 mM, dithiothreitol, 0.5 mM dGTP, 0.5 mM dCTP, 0.5 mM dTTP, 35 μM oligo dT primer (Amersham), 48 units of RAV-2 reverse transcriptase (RAV-2: Rous associated virus; Amersham) and 25 units of human placenta ribonuclease inhibitor (Amersham), and the mixture was incubated at 37° C. for 60 minutes, before being directly used in the following polymerase chain reaction (PCR).

3. Amplification of genes coding for antibody variable regions by PCR

PCR was carried out using a Thermal Cycler Model PHC-2 (Perkin Elmer Cetus).

(1) Amplification of gene coding for mouse L chain V region

Primers used for PCR were MKV (Mouse Kappa Variable) primers which hybridize with mouse kappa type L chain leader sequences and are shown in SEQ ID NOs: 1 to 11 (S. T. Jones et al., Biotechnology, 9, 88, 1991), and MKC (Mouse Kappa Constant) primer which hybridizes with the mouse κ type L chain c region and is shown in SEQ ID NO: 12 (S. T. Jones et al., Biotechnology, 9, 88, 1991).

100 μl of a PCR solution contained 10 mM Tris-HCl (pH 8.3), 50 mM KCl, 0.25 mM dNTPs (dATP, dGTP, dCTP, dTTP), 1.5 mM $MgCl_2$, 2.5 units of AmpliTaq DNA polymerase (Perkin Elmer Cetus), 0.25 μM of each MKV primer, 2.75 μM MKC primer and 1 μl of the reaction mixture for the generation of single-stranded cDNA. The mixture was overlaid with 50 μl of mineral oil, and heated at an initial temperature of 94° C. for 1.5 minutes, and then at 94° C. for 1 minute, 50° C. for 1 minute and 72° C. for 1 minute, in that order. This temperature cycle was repeated 25 times, and then the reaction mixture was further incubated at 72° C. for 10 minutes.

(2) Amplification of cDNA coding for mouse H chain V region

As primers for PCR, MHV (Mouse Heavy Variable) primers 1 to 12 shown in SEQ ID NOs: 13 to 24, and MHC-Gl (Mouse Heavy Constant) primer shown in SEQ ID NO: 25 (S. T. Jones et al., Biotechnology, 9, 88, 1991) were used.

Amplification of cDNA was carried out according to the same procedure as described in the above section 3. (1) for amplification of the L chain V region gene, except that the amplifications were separately carried out using a combination of 1 μM MHC-G1 primer and 1 μM of one of the MHV primers 1 to 12.

4. Purification and fragmentation of PCR products

The DNA fragments amplified as described above by PCR were purified with a low-melting agarose (FMC BioProducts, USA), and digested with 10 units of restriction enzyme SalI (GIBCO BRL) in 100 mM Tris-HCl (pH 7.6) containing 10 mM $MgCl_2$ and 150 mM NaCl at 37° C. for 3 hours.

The digestion mixtures were extracted with phenol and ethanol, and the DNA was recovered by ethanol precipitation. Next, the precipitated DNA was digested with 10 units of restriction enzyme XmaI (New England Biolabs) at 37° C. for 2 hours, and the resulting DNA fragments were separated by agarose gel electrophoresis using 1.5% low-melting agarose (FMC BioProducts, USA).

An agarose piece containing a DNA fragment of about 450 bp in length was cut out, and melted at 65° C. for 5 minutes, and the same volume of 20 mM Tris-HCl (pH 7.5) containing 2 mM EDTA and 200 mM NaCl was added thereto. This mixture was extracted with phenol and chloroform, and the DNA fragment was recovered by ethanol precipitation, and dissolved in 10 mM Tris-HCl (pH 7.5) containing 1 mM EDTA.

In this way, a DNA fragment containing a gene coding for a mouse Kappa type L chain V region, and a DNA fragment containing a gene coding for a mouse H chain V region were obtained. Both the above-mentioned DNA fragments have an SalI cohesive end at their 5'-terminus and an XmaI cohesive end at their 3'-terminus.

5. Ligation and transformation

About 0.3 μg of the SalI-XmaI DNA fragment comprising a gene coding for a mouse kappa type L chain V region prepared as described above was ligated into about 0.1 μg of pUC 19 vector prepared by digestion with SalI and XmaI in a reaction mixture containing 50 mM Tris-HCl (pH 7.4), 10 mM $gCl_2$, 10 mM dithiothreitol, 1 mM spermidine, 1 mM ATP, 0.1 μg/ml calf serum albumin and 2 units of T4 DNA ligase (New England Biolabs) at 16° C. for 16 hours.

Next, 7 μl of the ligation mixture was added to 200 μl of competent cells of E. coli DH5α, which were then allowed to stand on ice for 60 minutes, at 42° c. for one minute and again on ice for one minute. Next, 800 μl of SOC medium (Molecular Cloning: A Laboratory Manual, Sambrook et al., Cold Spring Harbor Laboratory Press, 1989) was added thereto, and after an incubation at 37° C. for one hour, the E. coli cells were plated on a 2X YT agar plate (Molecular Cloning: A Laboratory Manual, Sambrook et al., Cold Spring Harbor Laboratory Press, 1989), and incubated overnight at 37° C. to obtain E. coli transformants.

The transformants were cultured overnight in 5 ml of 2X YT medium containing 50 μg/ml ampicillin at 37° C., and from the culture was prepared a plasmid DNA according to an alkaline method (Molecular Cloning: A Laboratory Press, 1989).

The plasmid thus obtained containing a gene coding for a mouse kappa type L chain V region derived from hybridoma SK2 was designated pUC-SK2-$V_L$. p According to the same procedure as described above, a plasmid containing a gene coding for a mouse H chain V region derived from the hybridoma SK2 was constructed and amplified and designated pUC-SK2-$V_H$.

Example 2 Determination of nucleotide sequences of DNA

The nucleotide sequence of the cDNA coding regions in the above-mentioned plasmids were determined using a Sequenase™ version 2.0 kit (US Biochemical, USA).

First, about 3 μg of each plasmid obtained as described above was denatured with 0.2 N NaOH, annealed with a sequencing primer and labeled with $^{35}S$-dATP according to the manufacturer's instructions.

Next, the labeled DNA was subjected to electrophoresis on a 6% polyacrylamide gel containing 8 M urea, and the gel was fixed with 10% methanol and 10% acetic acid, dried, and subjected to radioautography for sequencing.

The nucleotide sequence of the gene coding for the mouse SK2 antibody L chain V region contained in the plasmid pUC-SK-$V_L$ is shown in SEQ ID NO: 26. In addition, the nucleotide sequence of the gene coding for the mouse SK2 antibody H chain V region contained in the plasmid pUC-SK2-$V_H$ is shown in SEQ ID NO.: 27.

Note that E. coli containing the plasmid pUC-SK2-$V_L$ designated Escherichia coli DH5α (pUC-SK2$V_L$) and E. coli containing the plasmid pUC-SK2-$V_H$ designated Escherichia coli DH5α (pUC-SK2$V_H$) were deposited with the National Institute of Bioscience and Human Technology Agency of Industrial Science and Technology (1–3 Higashi 1-chome, Tsukuba-shi, Ibaraki, Japan) on Apr. 21, 1993 as FERM BP-4270 and FERM BP-4269 respectively.

Example 3 Determination of CDRs the entire structures of the V regions of L and H chains have a mutual similarity, and in each V region, four framework regions are linked through three hypervariable regions, i.e., complementarity determining regions (CDRs). An amino acid sequence of a framework region is relatively well conserved, while an amino acid sequence of a CDR is highly variable (Kabat, E. A. et al. "Sequences of Proteins of Immunological Interest", US Dept. Health and Human Services, 1983)

Based on this fact, the amino acid sequences of the variable regions of mouse monoclonal antibody to human IL-6 were applied to a data base of amino acid sequences of antibodies, prepared by Kabat et al., and their homology was tested to determine the CDRs as shown in Table 4.

TABLE 4

| Plasmid | SEQ ID NO | CDR (1) | CDR (2) | CDR (3) |
|---------|-----------|---------|---------|---------|
| psk2-k2 | 27        | 24–34   | 50–56   | 89–96   |
| psk2-h1 | 29        | 31–37   | 52–67   | 100–109 |

Example 4 Confirmation of expression of cloned cDNA (Production of chimeric SK2 antibody)

Construction of expression vector

To construct expression vectors for chimeric SK2 antibodies, cDNA clones pUC-SK2-$V_L$ and pUC-SK2-$V_H$, coding for the mouse SK2 κL chain and H chain regions, respectively, were modified by the PCR method, and the cDNA was introduced into an HEF expression vector (see, WO92-19759, supra) (see, FIG. 1).

A backward primer for an L chain V region, SK2K2B (SEQ ID NO: 30), and a backward primer for an H chain V region, SK2H1S (SEQ ID NO: 32), were designed to hybridize with DNA coding for the beginning of the leader sequence of the corresponding V region, and have a Kozak consensus sequence (Kozak, M. et al., Mol. Biol. 196, 947–950, 1987) and a HindIII restriction site. A forward primer for an L chain V region, SK2K2A (SEQ ID NO: 31), and a forward primer for an H chain V region, 64hch-A (SEQ ID NO: 33), were designed to hybridize with a DNA sequence coding for the end of a J region, and have a splice donor sequence and a BamHI restriction site.

One hundred μl of a PCR mixture containing 10 mM Tris-HCl (pH 8.3), 50 mM KCl, 250 μM dNTPs, 1.5 mM MgCl$_2$, 100 pmoles of each primer, 100 ng template DNA (pUC-SK2-V$_L$ or pUC-SK2-V$_H$) and 5 units of AmpliTaq enzyme was overlaid with 50 μl of mineral oil, and after initial denaturation at 94° C., was subjected to 30 cycles incubation at 94° C. for one minute, 50° C. for one minute, and 72° C. for one minute, and finally incubated at 72° C. for 10 minutes.

The PCR products were purified on a 1.5% low melting agarose gel, digested with HindIII and BamHI, and subcloned into pUC19 vector (Yanishe-Perron et al., Gene (1985) 33: 103–109). After DNA sequencing, HindIII-BamHI fragments having the correct DNA sequence were excised, and the excised DNA for the H chain V region was introduced into the expression vector HEF-V$_{11}$-gγ1 to obtain HEF-SK2h-gγ1, and the excised DNA for the L chain V region was introduced into the expression vector HEF-V$_L$-gk to obtain HEF-SK2k-gk.

Regarding the H chain V region, in the H chain of most antibodies, the 30th residue, serine, is conserved, while in the H chain of the mouse SK2 antibody, the 30th amino acid is asparagine. Accordingly, to test the effect of this change on the antigen-binding activity of a chimeric SK2 antibody, the 30th residue, asparagine, was changed to serine by PCR mutagenesis using HEF-SK2h-gγ1 as a template, and a combination of the backward primer SK2H1S and the forward primer SK2HM1B (SEQ ID NO: 34) or a combination of the forward primer 64hch-A and the backward primer (SK2HM1) (SEQ ID NO: 35).

For the mutant H chain V region, PCR was carried out as described above using primers SK2H1S and SK2HM1B, or primers SK2HM1 and 64hch-A, and the plasmid HEF-SK2h-gγ1 as a template. After the PCR amplification, two PCR products were purified by low-melting agarose gel and used for the second PCR.

Ninety eight μl of a PCR mixture containing one μg of each of the two first PCR products and 5 units of AmpliTaq DNA polymerase was incubated at 94° C. for 2 minutes, 50° C. for 2 minutes and 72° C. for 5 minutes, and then 100 pmoles of each of the outer primers (SK2H1s and 64hch-A) were added thereto. The PCR mixture was overlaid with 50 μl of mineral oil, and the second PCR was carried out under the same conditions as described above. A DNA fragment of 412 bp was purified, digested with HindIII and BamHI, and inserted into an expression vector HEF-V$_H$-gγ1, and after sequencing, it was determined that a plasmid containing a correct sequence, HEF-SK2h-NTS, had been obtained.

Transfection of COS cells

To observe the transient expression of a chimeric SK2 antibody, the above-mentioned expression vectors were tested in COS cells. The HEF-SK2-gk, and either HEF-SK2h-gγ1 or HEF-SK2h-NTS were used to cotransfect COS cells by electroporation. Each DNA (10 μg) was added to 0.8 ml of a suspension of 1×10$^7$ cells/ml in PBS, and pulses at 1,900 V and a capacity of 25 μF were applied.

After recovery at room temperature for 10 minutes, the electroporated cells were added to DMEM culture solution (GIBCO) containing 10% γ-globulin-free bovine fetal serum, and containing or not containing 2 μg/ml tunicamycin (Sigma). After incubation for 72 hours, the culture medium was collected, centrifuged to eliminate cell debris, and applied to a protein A agarose column (Affi-Gel Protein A MAPSII kit, BioRad) equilibrated with 5 volumes of a binding buffer. The column was washed with the binding buffer. The column was washed with the binding buffer, and then elution was carried out with 5 volumes of an elution buffer. The eluate was concentrated, and the buffer was replaced with PBS using a microconcentrator (Centricon 100, Amicon).

ELISA

An ELISA plate for antigen-binding assay was prepared as follows. A 96-well plate was coated with mouse monoclonal antibody MH166 recognizing a different epitope of human IL-6 from that recognized by SK2 (Matsuda, T. et al., Eur. J. Immunol. 18, 951–956, 1988), and after blocking, recombinant human IL-6 was added thereto. A sample of the chimeric SK2 antibody was sequentially diluted, added to each well, and then an alkaline phosphatase-conjugated goat anti-human IgG antibody (Sigma) was added thereto. After incubation and washing, substrate was added, and absorbance at 405 nm was measured.

For binding-inhibition assay, an ELISA plate was prepared as follows. A 96-well plate was coated with mouse monoclonal antibody, MT-18 (Hirate, Y, et al., J. Immunol., 143, 2900–2907, 1989), specific to human IL-6 receptor (IL-6R), and, after blocking, soluble recombinant human IL-6R (SR344) (Yasukawa, K. et al. J. Biochem. 108, 673–676, 1990) was added thereto. A sample of this chimeric SK2 antibody was sequentially diluted, and added with biotinylated IL-6 to each well, and after adding an alkaline phosphatase-conjugated streptavidin thereto, absorbance at 405 nm was measured.

Figure 4:
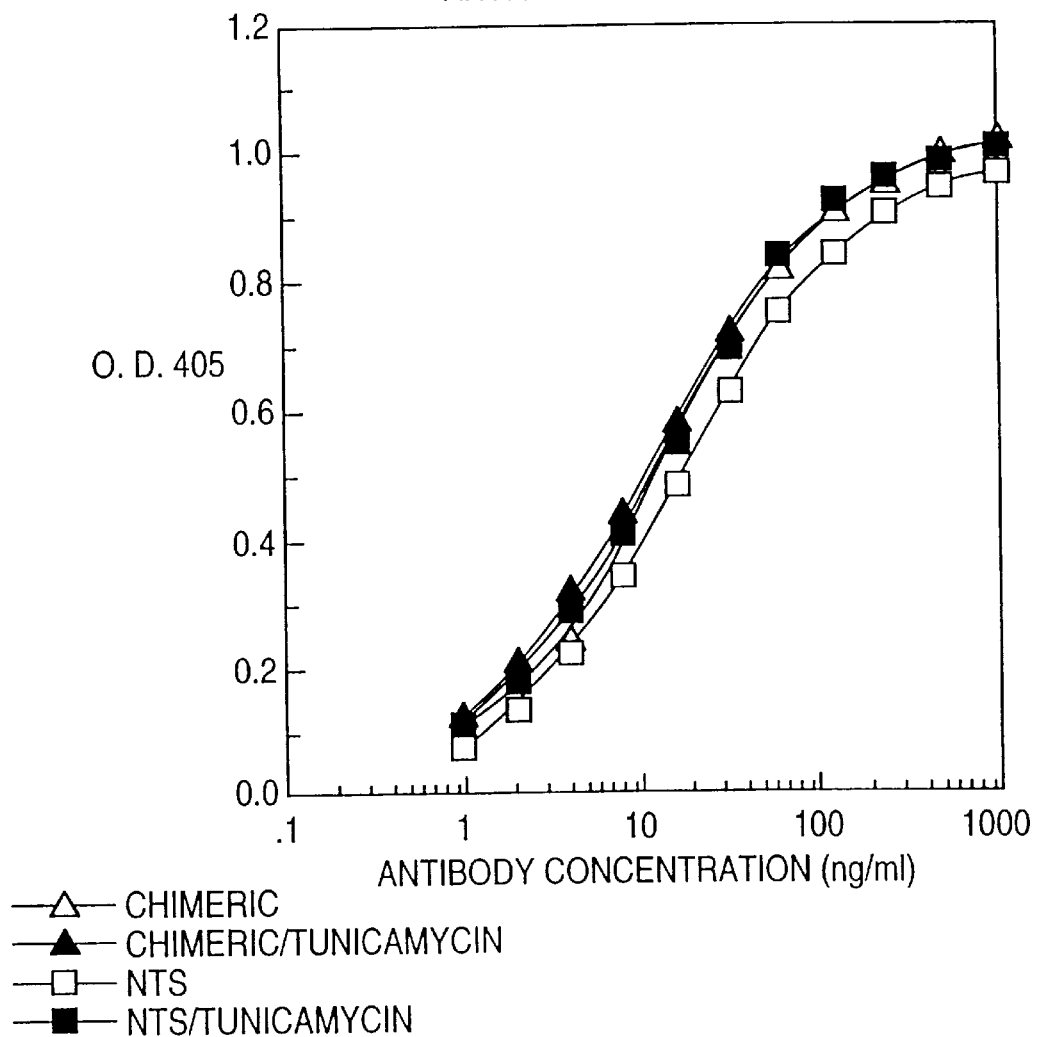
FIG. 4 is a graph representing the result of an ELISA for confirmation of the ability of the present chimeric antibody to bind to human IL-6.
Figure 5:
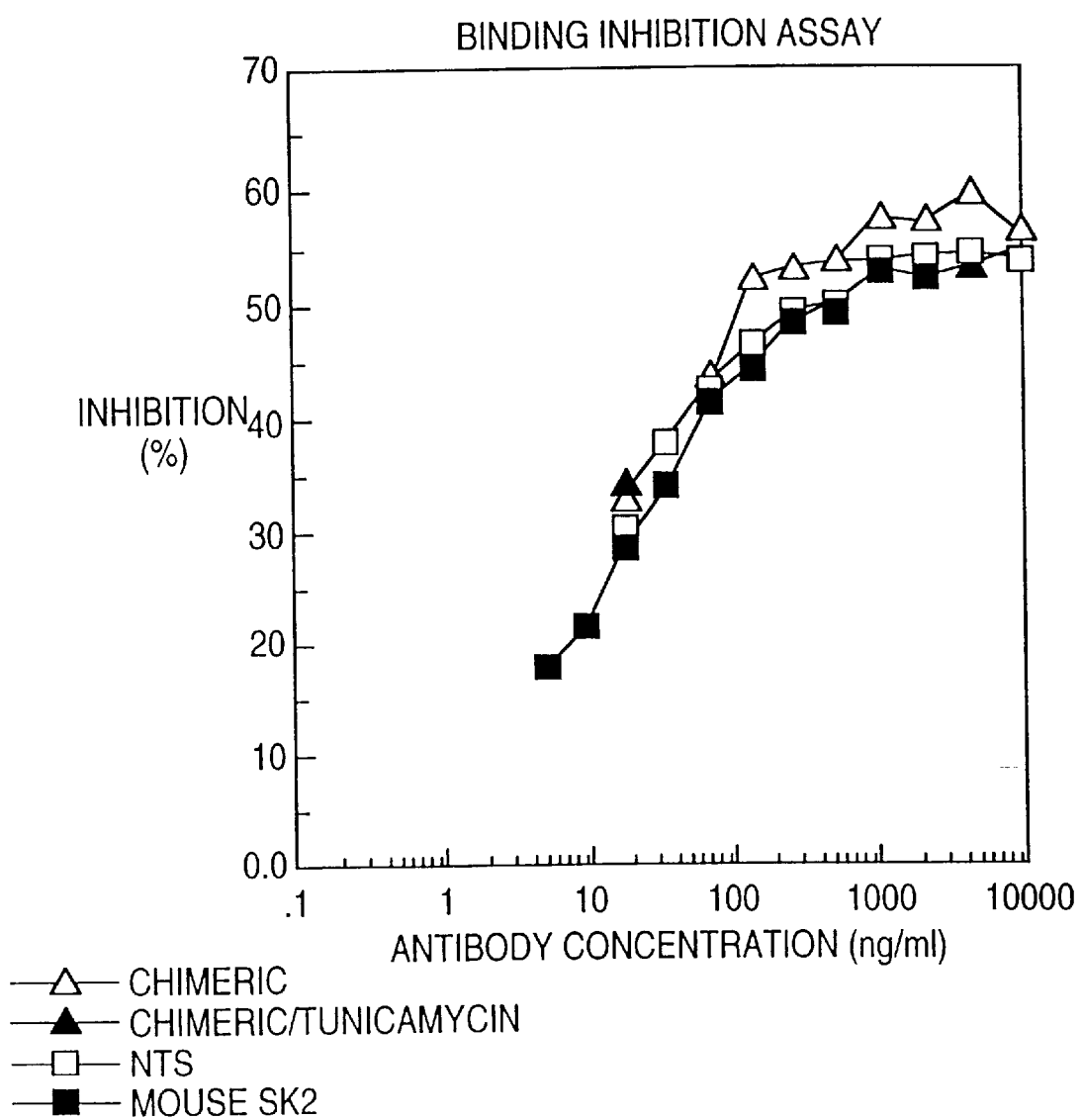
FIG. 5 is a graph representing the result of an ELISA for confirmation of the ability of the present chimeric antibody to inhibit the binding of IL-6 to human IL-6R.

The result of the antigen-binding assay is shown in FIG. 4, and the result of the binding-inhibition assay is shown in FIG. 5. A chimeric antibody wherein the 30th position of the H chain V region is asparagine, and a chimeric antibody (NTS) wherein the 30th position of H chain V region had been changed to serine exhibited similar antigen-binding and binding-inhibition without being affected by the inhibition of glycosylation by tunicamycin. Accordingly, it was established that the mutation of the 30th amino acid in the H chain V region and the presence or absence of sugar chains, do not exert any effect on antigen-binding.

Analysis of sugar chains of mouse SK2 antibody using SDS/PAGE and Western blotting Fab and Fc fragments were prepared from the mouse SK2 antibody using an ImmunoPure Fab Preparation kit (Pierce), and then deglycosylated fragments were prepared using N-Glycanase (Genzyme).

These fragments were subjected to SDS-polyacrylamide gel electrophoresis, and then stained with Coomassie Brilliant Blue (BioRad), or electrophoretically transferred to a nitrocellulose filter. To analyse the sugar attached to the Fd fragments, the filter was subjected to a panel of lectins (Lectine-Link, Genzyme).

Figure 3:
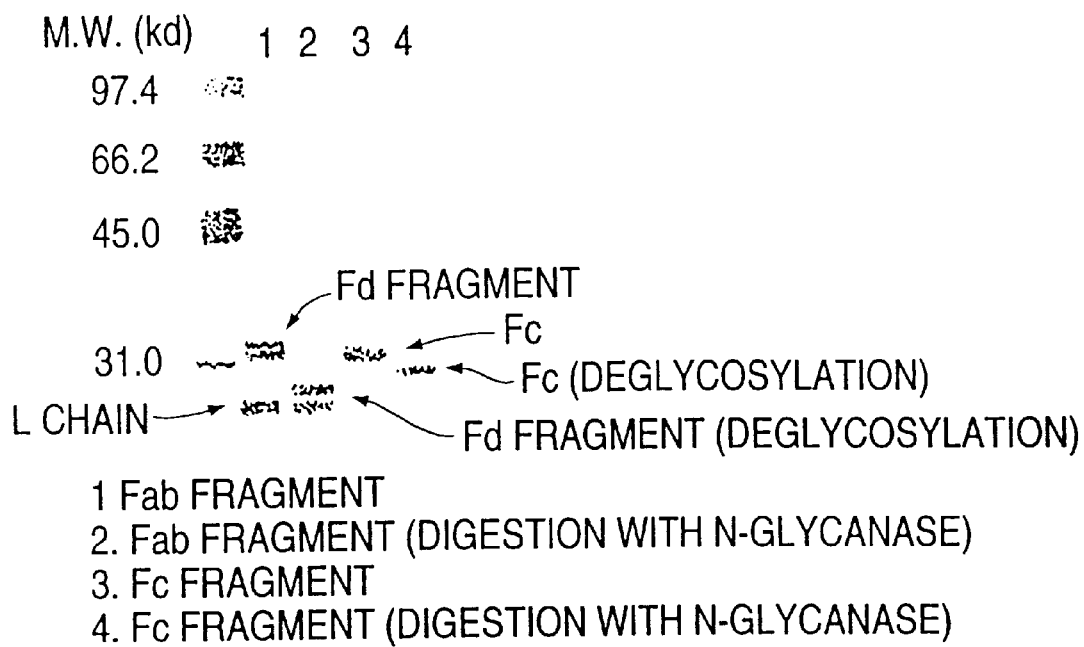
FIG. 3 is an electrophoresis profile showing that the SK2 antibody is glycosylated.

As shown in FIG. 3, Fd fragments from the mouse SK2 antibody exhibited bands of about 34 kd and 33 kd on SDS/PAGE, in a ratio of about 1:1. Fd fragments deglycosylated with N-glycanase exhibited a molecular weight of about 29 kd, which conformed to the values calculated from the amino acid compositions of the Fd fragments. In addition, the 34 kd Fd fragment and the 33 kd Fd fragment showed different reactivities to various lectins.

Namely, the 34 kd Fd showed reactivities to Datura Stramonium Agglutinin (DSA)$^+$, Ricinus Communis Agglutinin (RCA)$^{++}$, Phaseolus Vulgaris Erythrolectin (PHA-E)$^{+++}$, Concanavalin A (Con A)-, and Wheat Germ Agglutinin (WGA)$^+$, while the 33 kd Fd showed reactivities of DSA-RCA$^+$, PHA-E$^{+++}$, con A-, and WGA-. From these results, it was established that the mouse SK2 antibody has at least 2 different types of N-type sugar chain in the H chain V region.

Example 5 Construction of reshaped human SK2 antibodies

Figure 6:
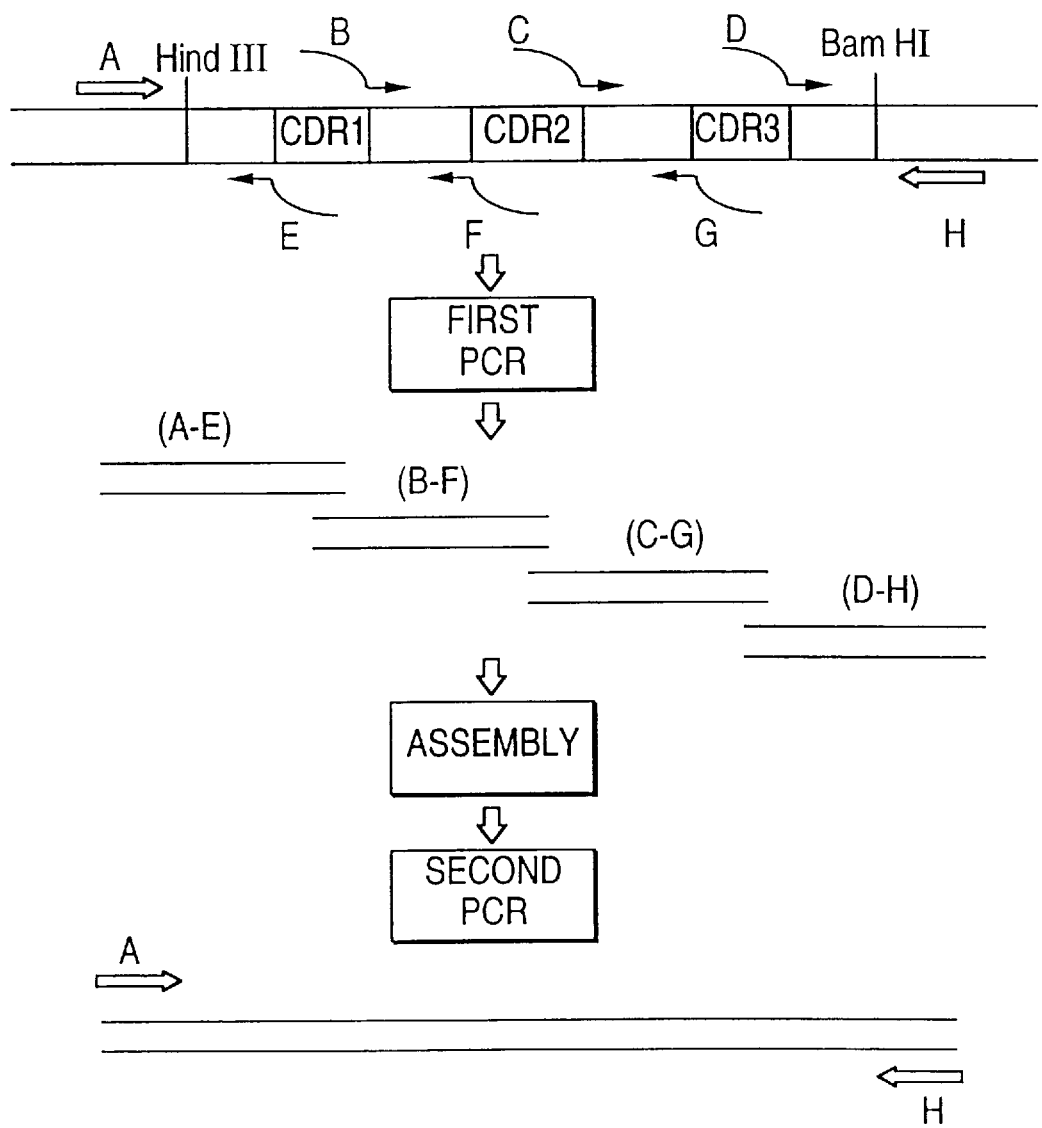
FIG. 6 is a diagram for the construction of the first version (version "a") of the L chain V region of a reshaped human SK2 antibody.

Construction of L chain V region of reshaped human SK2 an L chain of a reshaped human SK2 antibody was constructed by CDR-grafting using the PCR method. This process is shown schematically in FIG. 6. Eight PCR primers were used to construct reshaped human antibody SK2 (version "a") having FRs derived from the human antibody REI. The outer primers A (SEQ ID NO: 36) and H (SEQ ID NO: 37) were designed to hybridize with DNA sequences of the pUC vector.

CDR-grafting primers B (SEQ ID NO: 38), C (SEQ ID NO: 39) and D (SEQ ID NO: 40) have sense DNA sequences; and CDR-grafting primers E (SEQ ID NO: 34), F (SEQ ID NO: 42) and G (SEQ ID NO: 43) have antisense DNA sequences, and have DNA sequence (15 and 30 bp) complementary to the 5'-terminus of the primers B, C and D, respectively.

In the first PCR step, four reactions A–E, B–F, C–G, and D–H were carried out separately, and each PCR product was purified. The four PCR products from the first PCR were assembled by their own complementarity (see, WO92-19759). Next, the outer primers A and H were added to amplify an entire DNA coding for the L chain V region of a reshaped human SK2 antibody (second PCR). In this PCR, plasmid pUV-RVL-PM1a-4 (see, WO92-19759) coding for L chain V region version "a" of reshaped human PM-1 antibody, based on FRs from human antibody REI, was used as a template.

In the first PCR step, 100 $\mu$l of a PCR mixture containing 10 mM Tris-HCl (pH 8.3), 50 mM KCl, 250 $\mu$M dNTPs, 1.5 mM $MgCl_2$, 100 ng of the template DNA, 100 pmoles of each primer and 5 units of AmpliTaq DNA polymerase was used. Each PCR tube was overlayered with 50 $\mu$l of mineral oil. First, after denaturation at 94° C., reaction cycles of 94° C. for one minute, 50° C. or 55° C. for one minute and 72° C. for one minute were carried out, and then an incubation at 72° C. for 10 minutes was carried out.

The PCR products A–E (187 bp), B–F (87 bp), C–G (152 bp) and D–E (65 bp) were purified on a 1:5% low melting agarose gel, and assembled in the second PCR. In the second PCR, 98 $\mu$l of PCR mixture containing 1 $\mu$g of each of the first PCR products and 5 units of AmpliTaq DNA polymerase was incubated in two cycles of 94° C. for 2 minutes, 50° C. for 2 minutes and 72° C. for 2 minutes, and then 100 pmoles of each outer primer (A and H) was added thereto. The PCR tube was overlaid with 50 $\mu$l of mineral oil, and 30 cycles of PCR were carried out under the same conditions as described above.

A DNA fragment of 399 bp generated in the second PCR was purified on a 1.5% low melting agarose gel, and digested with BamHI and HindIII, and the resulting DNA fragment was cloned into the HEF expression vector, HEF-$V_L$-gk. After DNA sequencing, a plasmid containing a DNA fragment coding for the correct amino acid sequence of L chain V region version "a" of reshaped human SK2 antibody was designated HEF-RVL-SK2a. The amino acid sequence of, and nucleotide sequence for, the L chain V region contained in the plasmid HEF-RVL-SK2a are shown in SEQ ID NO: 54–55.

L chain V region version "b" of reshaped human SK2 antibody was constructed by mutagenesis using PCR. The mutagenic primers FTY-1 (SEQ ID NO: 44) and FTY-2 (SEQ ID NO: 45) were designed so that the 71st amino acid residue, phenylalanine, was mutated to tyrosine. Plasmid HEF-RVL-SK2a was used as the template. The final PCR product was purified, and digested with BamHI and HindIII, and the resulting DNA fragment was cloned into an HEF-expression vector, HEF-$V_L$-gk, to obtain plasmid HEF-RVL-SK2b. The amino acid sequence of, and nucleotide sequence for, the L chain V region contained in the plasmid HEF-RVL-SK2b are shown in SEQ ID NO: 56–57.

Construction of H chain V region of reshaped human SK2 antibody

A DNA coding for the H chain V region of reshaped human SK2 antibody was designed as follows. DNA sequences coding for the FRs of human antibody DAW were designed on the basis of "codon usage" of the V region (Kabat, E. A. et al., U.S. Dept. Health and Human Services, U.S. Government Printing Offices, 1991), and joined to DNA sequences coding for the CDRs of the H chain V region of the mouse SK2 antibody to result in a full-length DNA coding for H chain V region version "a" of reshaped human SK2 antibody.

Next, a HindIII restriction site/KOZAK consensus sequence and a BamHI restriction site/splice donor sequence were added to the 5'-side and the 3'-side, respectively, of the above-mentioned DNA sequence so as to allow the insertion thereof into an HEF expression vector.

The DNA sequence thus designed was prepared as 6 oligonucleotides, and a computer analysis was then carried out regarding the secondary structure of each to determine if there was any danger of interference with their subsequent assembly.

Figure 7:
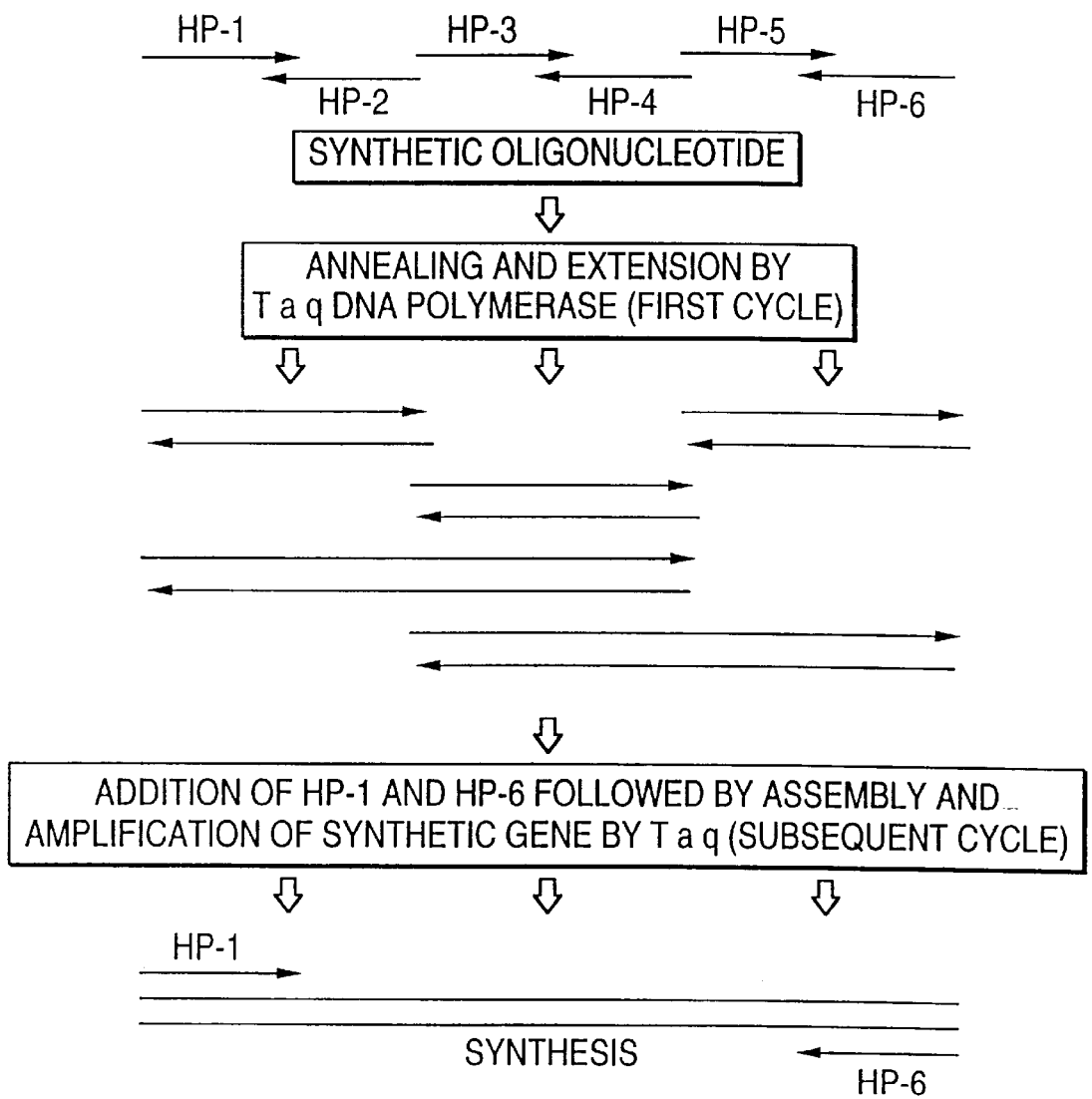
FIG. 7 is a diagram for the construction of the first version (version "a") of the H chain V region of a reshaped human SK2 antibody.

The six oligonucleotide sequences are shown in SEQ ID NOs: 46 to 51. These oligonucleotides have a 93 to 98 nucleotide length with 20 to 24 bp overlapping regions. Among these oligonucleotides, three nucleotides, i.e., HP1 (SEQ ID NO: 46), HP3 (SEQ ID NO: 48) and HP5 (SEQ ID NO: 50) have a sense DNA sequence, and the other three oligonucleotides, i.e., HP2 (SEQ ID NO: 47), HP4 (SEQ ID NO: 49) and HP6 (SEQ ID NO: 51) have an antisense DNA sequence. A process for the assembly of these 6 oligonucleotides by the PCR method is shown in FIG. 7.

Ninety eight $\mu$l of PCR mixture containing 2 pmoles of each of the 6 oligonucleotides and 5 units of DNA polymerase was, after a first denaturation at 94° C. for 2 minutes, subjected to 3 cycles of incubation consisting of 94° C. for one minute, 50° C. for one minute and 72° C. for one minute, followed by an incubation at 72° C. for 10 minutes. 50 pmole each of HP1 and HP6 were added as the outer primers, the PCR tube was overlaid with 50 $\mu$l of mineral oil, and after a first denaturation at 94° C. for one minute, 30 cycles of incubation at 94° C. for one minute, 50° C. for one minute and 72° C. for one minute were carried out, followed by incubation at 72° C. for 10 minutes.

A DNA fragment of 448 bp was purified with a 1.5% low-melting agarose gel, digested with HindIII and BamHI, and then cloned into an HEF expression vector, HEF-$V_H$-gyl. After DNA sequencing, a plasmid containing a DNA fragment coding for the correct amino acid sequence of the H chain V region was designated HEF-RVH-SK2a. The amino acid sequence of, and nucleotide sequence for the H chain V region contained in the plasmid HEF-RVH-SK2a is shown in SEQ ID NO: 58–59.

Version "b" was constructed by mutagenesis using the PCR method. The mutegenic primers RSK-STNA (SEQ ID NO: 52) and RSK-STNB (SEQ ID NO: 53) were designed so that the 30th amino acid residue, serine, was changed to asparagine. The plasmid RVH-SK2a was used as template DNA. The final PCR product was purified, digested with BamHI and HindIII, and cloned into the HEF expression vector HEF-V$_H$-gγ1 to obtain the plasmid HEF-RVH-SK2b. The amino acid sequence of, and nucleotide sequence for, the H chain V region contained in the plasmid HEF-RVH-SK2b are shown in SEQ ID NO: 20–51.

To assess each chain of a reshaped human SK2 antibody, first, COS cells were co-transfected with one of the two expression vectors for reshaped human SK2 antibody L chain i.e., HEF-RVL-SK2a (version "a") and HEF-RVL-SK2b (version "b"), and with an expression vector for the chimeric SK2 antibody H chain, HEF-SK2h-gγ1, and the antibody product was recovered as described above, and subjected to an antigen-binding assay.

Figure 8:
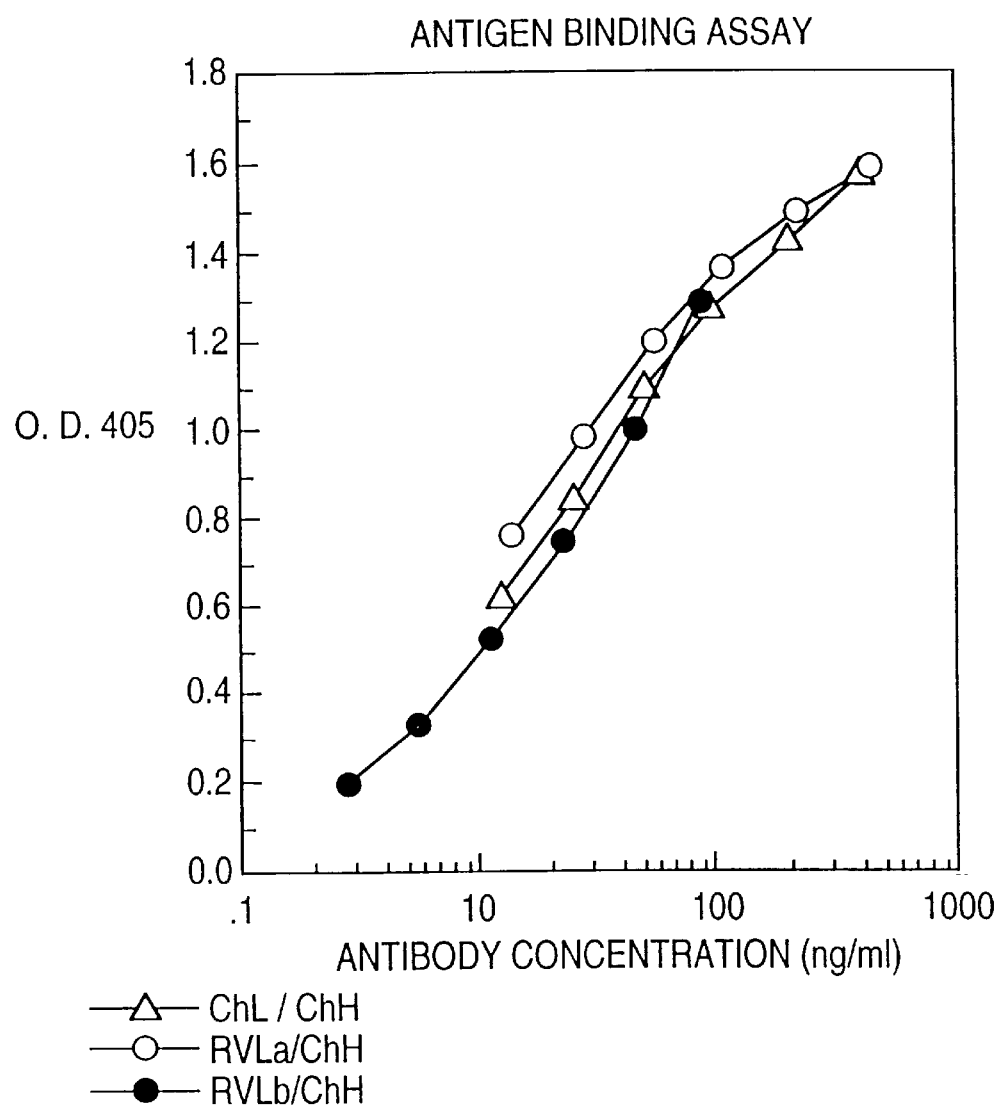
FIG. 8 is a graph representing the ability of an antibody comprising reshaped human L chains and chimeric H chains to bind to human IL-6.

The result is shown in FIG. 8. As shown in FIG. 8, there is no difference in antigen-binding ability between a chimeric antibody (ChL/ChH) as a positive control, an antibody comprising reshaped L chain version "a" and chimeric H chain (RVLa/ChH), and an antibody comprising reshaped L chain version "b" and chimeric H chain (RVLb/ChH) demonstrating that the change of the 71st tyrosine residue to a phenylalanine residue does not affect antigen-binding ability.

Figure 9:
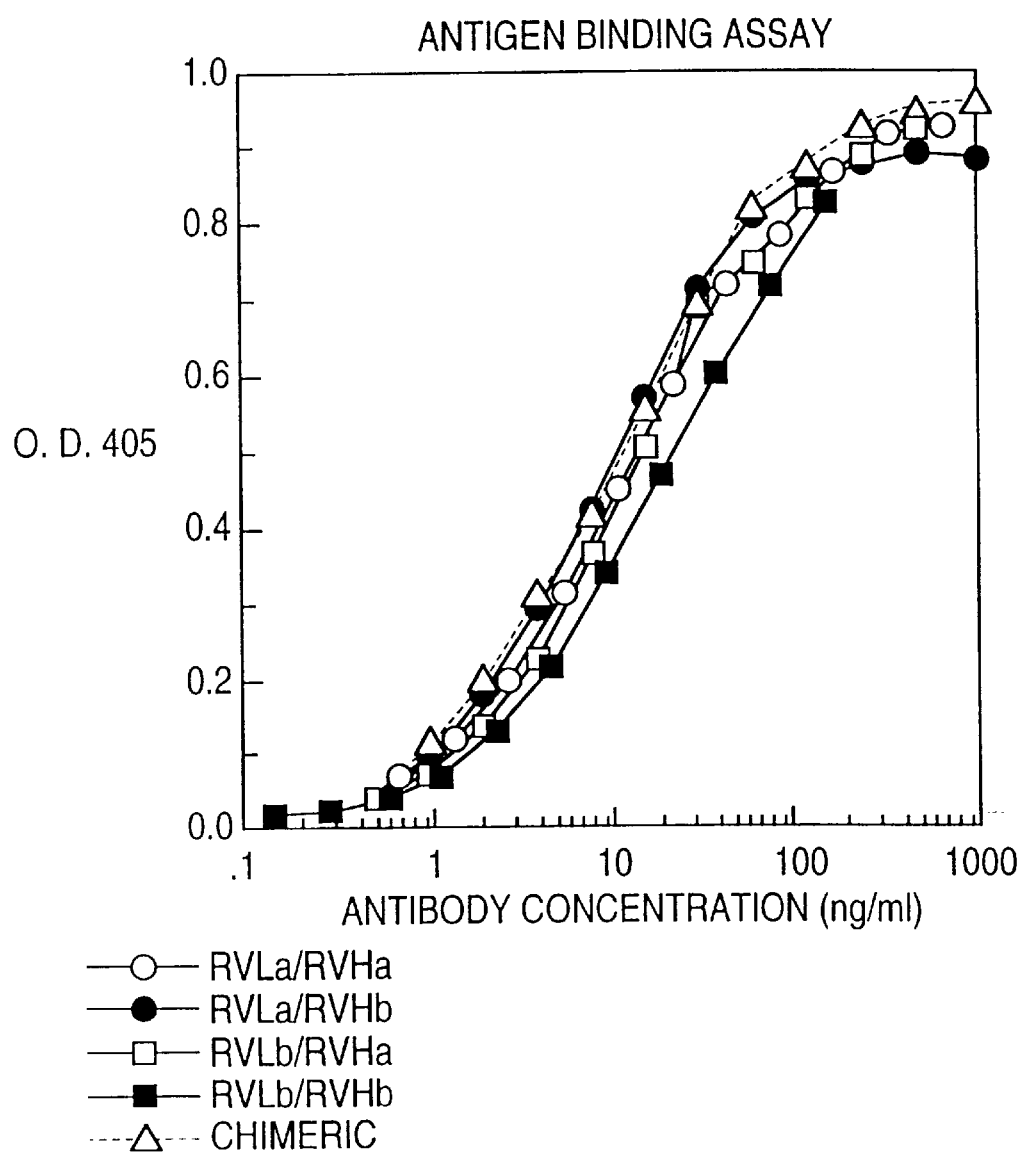
FIG. 9 is a graph comparing the abilities of four reshaped human SK2 antibodies of the present invention with that of a chimeric antibody to bind to human IL-6.

Next, to assess the combination of two versions of reshaped human SK2 antibody L chain and two versions of reshaped human SK2 antibody H chain, COS cells were co-transfected with HEF-RVL-SK2a and RVH-SK2a, HEF-RVL-SK2a and RVH-SK2b, HEF-RVL-SK2b and RVH-SK2a, or HEF-RVL-SK2b and RVH-SK2b, and antigen-binding assay was carried out for the resulting antibodies, as described above. The result is shown in FIG. 9. As can be seen from FIG. 9, all combinations of reshaped human H chains and reshaped human L chains exhibited good antigen-binding ability, which was comparable to that of the chimeric SK2 antibody.

Note, *E. coli* containing the plasmid HEF-RV$_L$-SK2b, designated *Escherichia coli* DH5α (HEF-RV$_L$-SK2b), and *E. coli* containing the plasmid HEF-RV$_H$-SK2a, designated *Escherichia coli* DH5α (HEF-RV$_H$-SK2a) were deposited with the National Institute of Bioscience and Human Technology Agency of Industrial Science and Technology (1–3, Higashi 1-chome, Tsukuba-shi, Ibaraki, Japan) on Apr. 21, 1993 as FERM BP-4267 and FERM BP-4268 respectively, as international depositions under the Budapest treaty.

On the contrary, as shown in FIG. 10, in binding-inhibition (ability of an antibody to inhibit binding of IL-6 and IL-6R) assay, only a combination of the reshaped human SK2 antibody L chain version "b" (RvLb) and the reshaped human SK2 antibody H chain version "a" (RvHa) exhibited a binding-inhibition ability comparable to that of mouse monoclonal antibody SK2 and the chimeric SK2 antibody, suggesting that this combination forms a functional antigen-binding site in a human antibody.

On the other hand, the combination of the reshaped human SK2 antibody L chain version "a" (RvLa) and the reshaped human SK2 antibody H chain version "a" (RvHa), and the combination of RvLa and RvHb exhibited a low binding inhibition activity, suggesting that although an antibody having phenylalanine at the 71st position of the L chain exhibits good antigen-binding activity, it does not reform a functional antigen-binding site.

From these facts, it can be deduced that in the loop structure in the CDR1 region of a human antibody L chain, the 71st tyrosine is essential for the reformation of a functional antigen-binding site.

REFERENCE EXAMPLE 1

Construction of Hybridoma SK2

A hybridoma producing an anti-human IL-6 monoclonal antibody was constructed by fusing the spleen cells of a BALB/c mouse immunized with human IL-6 with mouse myeloma cell line P3U1 according to conventional procedures using polyethylene glycol. Screening for the inhibition of binding of IL-6 and IL-6R was carried out to obtain 17 clones having binding-inhibitory activity. These clones were intraperitoneally transplanted to mice, and the ascites was applied to a Protein A agarose column to obtain purified mouse monoclonal antibody.

REFERENCE EXAMPLE 2

Typing of Mouse Monoclonal Antibody SK2

To determine the type of L chain and H chain of the mouse monoclonal antibody SK2 produced by hybridoma SK2, typing was carried out using a Mouse Monoclonal Antibody Isotyping Kit (Amersham International plc). As a result, it was found that the SK2 antibody has κ type L chains and γ1 H chains.

Reference to deposited microorganisms under 13-2 of PCT as well as the name and address of the depository authority.

National Institute of Bioscience and Human
Technology Agency of Industrial Science and
Technology 1–3, Higashi, 1-chome, Tsukuba-shi, Ibaraki, Japan

| | Deposition No. | Date of deposition |
|---|---|---|
| 1. *E. coli* DH5α (HEF-RV$_L$-SK2b) | FERM BP-4267 | April 21, 1993 |
| 2. *E. coli* DH5α (HEF-RV$_H$-SK2a) | FERM BP-4268 | April 21, 1993 |
| 3. *E. coli* DH5α (pUC-SK2V$_H$) | FERM BP-4269 | April 21, 1993 |
| 4. *E. coli* DH5α (pUC-SK2V$_L$) | FERM BP-4270 | April 21, 1993 |

What is claimed is:

1. An isolated polypeptide light (L) chain of an antibody to human interleukin-6, wherein the L chain comprises an L chain variable (V) region and a human L chain constant (C) region; wherein the L chain V region is represented by the formula (I):

FRL1-CDRL1-FRL2-CDRL2-FRL3-CDRL3-FRL4 wherein the FRL1, FRL2, FRL3 and FRL4 have the following amino acid sequences respectively:
  FRL1: Asp Ile Gln Met Thr Gln Ser Pro Ser Ser Leu Ser Ala Ser Val Gly Asp Arg Val Thr Ile Thr Cys (SEQ ID NO: 69);
  FRL2: Trp Tyr Gln Lys Pro Gly Lys Ala Pro Lys Leu Leu Ile Tyr (SEQ ID NO: 70);
  FRL3: Gly Val Pro Ser Arg Phe Ser Gly Ser Gly Ser Gly Thr Asp Tyr Thr Phe Thr Ile Ser Ser Leu Gln Pro Glu Asp Ile Ala Thr Tyr Tyr Cys (SEQ ID NO: 71); and
  FRL4: Phe Gly Gln Gly Thr Lys Val Glu Ile Lys (SEQ ID NO: 72);
and the CDRL1, CDRL2 and CDRL3 have the following amino acid sequences respectively;
  CDRL1: Arg Ala Ser Glu Asn Ile Tyr Ser Asn Leu Ala (SEQ ID NO: 62)
  CDRL2: Ala Ala Thr Tyr Leu Ala Asp (SEQ ID NO: 63)
  CDRL3: Gln His Phe Trp Gly Thr Pro Pro (SEQ ID NO: 64)

or
wherein the L chain V region comprises a polypeptide encoded by the nucleotide sequence shown in SEQ ID NO: 56.

2. An isolated polypeptide comprising
  (i) a light (L) chain of an antibody to human interleukin-6, wherein the L chain comprises an L chain variable (V) region and a human L chain constant (C) region; wherein the L chain V region is represented by the formula (I):

FRL1-CDRL1-FRL2-CDRL2-FRL3-CDRL3-FRL4 wherein the FRL1, FRL2, FRL3 and FRL4 have the following amino acid sequences respectively:
  FRL1: Asp Ile Gln Met Thr Gln Ser Pro Ser Ser Leu Ser Ala Ser Val Gly Asp Arg Val Thr Ile Thr Cys (SEQ ID NO: 69);
  FRL2: Trp Tyr Gln Gln Lys Pro Gly Lys Ala Pro Lys Leu Leu Ile Tyr (SEQ ID NO: 70);
  FRL3: Gly Val Pro Ser Arg Phe Ser Gly Ser Gly Ser Gly Thr Asp Tyr Thr Phe Thr Ile Ser Ser Leu Gln Pro Glu Asp Ile Ala Thr Tyr Tyr Cys (SEQ ID NO: 71); and
  FRL4: Phe Gly Gln Gly Thr Lys Val Glu Ile Lys (SEQ ID NO: 72);
and the CDRL1, CDRL2 and CDRL3 have the following amino acid sequences respectively;
  CDRL1: Arg Ala Ser Glu Asn Ile Tyr Ser Asn Leu Ala (SEQ ID NO: 62)

CDRL2: Ala Ala Thr Tyr Leu Ala Asp (SEQ ID NO: 63)

CDRL3: Gln His Phe Trp Gly Thr Pro Pro (SEQ ID NO: 64)

or wherein the L chain V region comprises a polypeptide encoded by the nucleotide sequence shown in SEQ ID NO: 56;

and (ii) a heavy (H) chain of an antibody to human interleukin-6, wherein the H chain comprises an H chain V region and a human H chain C region wherein the H chain V region is represented by the formula (II):

FRH1-CDRH1-FRH2-CDRH2-FRH3-CDRH3-FRH4 wherein the FRH1, FRH2, FRH3 and FRH4 have one of sets ((a) or (b)) of the following amino acid sequences respectively:

(a) FRH1: Gln Val Thr Leu Arg Glu Ser Gly Pro Ala Leu Val Arg Pro Thr Gln Thr Leu Thr Leu Thr Cys Thr Phe Ser Gly Phe Ser Leu Ser (SEQ ID NO: 76);

FRH2: Trp Ile Arg Gln Pro Pro Gly Glu Ala Leu Glu Trp Leu Ala (SEQ ID NO: 77);

FRH3: Arg Leu Ala Val Ser Lys Asp Thr Ser Lys Asn Gln Val Val Leu Ser Met Asn Thr Val Gly Pro Gly Asp Thr Ala Thr Tyr Tyr Cys Ala Arg (SEQ ID NO: 78);

and

FRH4: Trp Gly Gln Gly Ile Leu Val Thr Val Ser Ser (SEQ ID NO: 79) or (b) FRH1: Gln Val Thr Leu Arg Glu Ser Gly Pro Ala Leu Val Arg Pro Thr Gln Thr Leu Thr Leu Thr Cys Thr Phe Ser Gly Phe Ser Leu Asn (SEQ ID NO.: 80);

FRH2: Trp Ile Arg Gln Pro Pro Gly Glu Ala Leu Glu Trp Leu Ala (SEQ ID NO.: 81);

FRH3: Arg Leu Ala Val Ser Lys Asp Thr Ser Lys Asn Gln Val Val Leu Ser Met Asn Thr Val Gly Pro Gly Asp Thr Ala Thr Tyr Tyr Cys Ala Arg (SEQ ID NO: 82);

and

FRH4: Trp Gly Gln Gly Ile Leu Val Thr Val Ser Ser (SEQ ID NO: 83);

and the CDRH1, CDRH2, and CDRH3 have the following amino acid sequences respectively:

CDRH1: Thr Ser Gly Met Thr Val Gly (SEQ ID NO: 73);

CDRH2: His Ile Trp Trp Asn Asp Asp Lys Tyr Tyr Asn Pro Ala Leu Lys Gly (SEQ ID NO: 74);

CDRH3: Met Glu Asp Tyr Asp Glu Ala Met Asp Tyr (SEQ ID NO: 75) or wherein the H chain V region comprises a polypeptide encoded by the nucleotide sequence shown in SEQ ID NO: 60.

3. The isolated polypeptide according to claim 1, wherein the L chain V region comprises a polypeptide encoded by the nucleotide sequence of SEQ ID NO: 56.

* * * * *